(12) United States Patent
Ghaedian et al.

(10) Patent No.: US 8,557,305 B2
(45) Date of Patent: Oct. 15, 2013

(54) COMPOSITIONS AND METHODS FOR CONTROLLING METABOLIC SYNDROME USING WHOLE FRUIT-DERIVED CRANBERRY INGREDIENT PROFILE ENRICHED IN STRESS ADAPTED BIOACTIVES (SABS)

(75) Inventors: Reza Ghaedian, Plymouth, MA (US); Rahul M. Shinde, New Bedford, MA (US); Kalidas Shetty, Amherst, MA (US)

(73) Assignee: Decas Botanical Synergies, LLC, Carver, MA (US)

( * ) Notice: Subject to any disclaimer, the term of this patent is extended or adjusted under 35 U.S.C. 154(b) by 0 days.

(21) Appl. No.: 13/431,123

(22) Filed: Mar. 27, 2012

(65) Prior Publication Data

US 2012/0251636 A1    Oct. 4, 2012

Related U.S. Application Data

(63) Continuation of application No. 12/698,262, filed on Feb. 2, 2010, now Pat. No. 8,173,178, which is a continuation-in-part of application No. 12/184,934, filed on Aug. 1, 2008, now abandoned.

(60) Provisional application No. 60/953,845, filed on Aug. 3, 2007.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

2008/0020094 A1 *   1/2008   Lager .............................. 426/50

* cited by examiner

*Primary Examiner* — Michael Meller
(74) *Attorney, Agent, or Firm* — Hiscock & Barclay, LLP

(57) ABSTRACT

Compositions of a whole fruit-derived cranberry ingredient profile, enriched in Stress Adapted Bioactive (SABs) from cranberries are described, for use in reducing the blood glucose level of diabetic, prediabetic, or other hyperglycemic individuals and individuals having one or more metabolic syndrome related factors. The compositions are prepared from whole fruit-derived cranberry pomace, which may be liquid or powdered, and which is enriched in Stress Adapted Bioactives (SABs) and enriched in soluble polyphenolics. Methods for using whole cranberry ingredient profile, enriched in polyphenolic-containing SABs, for the management of individuals having one or more symptoms of metabolic syndrome and for minimizing the effects of the syndrome are disclosed.

1 Claim, 15 Drawing Sheets

COMPOSITIONS AND METHODS FOR CONTROLLING METABOLIC SYNDROME USING WHOLE FRUIT-DERIVED CRANBERRY INGREDIENT PROFILE ENRICHED IN STRESS ADAPTED BIOACTIVES (SABS)

CROSS REFERENCE TO RELATED APPLICATIONS

The present application is a continuation of U.S. application Ser. No. 12/698,262, filed Feb. 2, 2010 (now U.S. Pat. No. 8,173,178 issued May 8, 2012), which in turn is a continuation-in-part of U.S. application Ser. No. 12/184,934, filed Aug. 1, 2008 (abandoned), which in turn claims the benefit of U.S. Provisional Application Ser. No. 60/953,845, filed Aug. 3, 2007. Each of these related applications is hereby incorporated by reference in its entirety.

TECHNICAL FIELD

The present invention relates to soluble whole fruit cranberry ingredient profiles enriched in polyphenolic-containing SABs and more particularly to the manufacture and use of enriched polyphenolic-containing SABs. Still more particularly, the claimed invention relates to enriched polyphenolic-containing SABs from cranberry pomace for controlling blood glucose, blood pressure and plasma lipids, for reducing the risk of development of metabolic syndrome, and for managing individuals with one or more symptoms of metabolic syndrome.

BACKGROUND

Metabolic syndrome is the collective presence of symptoms related to insulin resistance, glucose intolerance, dyslipidemia, high cholesterol, hypertension, and abdominal obesity. These symptoms, when present in different combinations and different levels, increase the risk of cardiovascular diseases. Metabolic syndrome related symptoms are also good indicators of prediabetic conditions in individuals.

To determine the presence of metabolic syndrome in individuals, physicians can use more than one definition, like one put forth by the World Health Organization ("WHO") or by the Adult Treatment Panel III ("ATP-III"), or by the International Diabetes Federation. The diagnosis is based on the presence of a combination of metabolic disorders. For example, according to WHO, a person should have glucose intolerance or diabetes and two of the following three disorders: waist to hip ratio >0.9, BMI >30 or triacylglycerols >150 mg/dl or blood pressure >140/90 mm of Hg or albumin to creatine ratio of 30 mg/g. Using the most recent and well-accepted definition provided by the ATP-III (≥3 of the following abnormalities), metabolic syndrome is defined as: waist circumference greater than 102 cm in men and 88 cm in women; serum triglyceride levels of at least 150 mg/dl; high density lipoprotein cholesterol level of less than 40 mg/dl in men and 50 mg/dl in women; blood pressure of at least 130/85 mm of Hg; or serum glucose level of at least 110 mg/dl.

Since the condition is a combination of various components, symptoms or disorders, the diagnosis is not absolute and would be expected to differ depending on the definition used, the dynamics of the population and the physicians conducting the diagnosis. Due to the lack of a standardized set of criteria, it is difficult to understand the prevalence of metabolic syndrome. The overall prevalence of metabolic syndrome in U.S. adults is 20-24%. There is an upward trend of the prevalence of metabolic syndrome with increasing age. The prevalence is 7% in the 20 to 29 age group and as high as 40-45% in the 60 to 69 and over 70 yrs age group. African-American women have a 57% higher prevalence rate then African-American men. Using 2000 census data, about 47 million U.S. residents have the metabolic syndrome (Cook et al, 2008 and Ford et al, 2002). Prevalence outside the U.S. has been observed at 15% in Europe, 7% in Korea, 30% in Iran and 32% in India.

Metabolic Syndrome—Disease Components, Symptoms and Risk Factors Diabetes and Prediabetes Diabetes is both a component and effect of metabolic syndrome. There are several different classifications of diabetes. For example, type 1 diabetes results from the body's failure to produce insulin, the hormone responsible for metabolism of sugar. It is estimated that 5-10% of Americans who are diagnosed with diabetes have type 1 diabetes. Gestational diabetes affects about 4% of all pregnant women, or approximately 135,000 cases in the United States each year.

Type 2 diabetes results from insulin resistance (a condition in which the body fails to properly use insulin), combined with relative insulin deficiency. Most Americans who are diagnosed with diabetes have type 2 diabetes. Of the key types of diabetes, type 2 is most frequently spotlighted because it is essentially preventable. This disease is deemed largely preventable by the medical community because it is understood to be a result of a lifestyle fraught with poor dietary habits, infrequent or no exercise, and other factors.

Pre-diabetes is a condition that occurs when a person's blood glucose levels are higher than normal but not high enough for a diagnosis of type 2 diabetes. There are 41 million Americans who have pre-diabetes, in addition to the 20.8 million with diabetes. For the 41 million Americans suffering from pre-diabetes—a precursor to diabetes type 2—the American Diabetes Association (ADA) recommends lifestyle modifications, including dietary supplementation, to treat the condition and alleviate its adverse effects.

Pre-diabetes is a more recently used term to describe the state of elevated blood glucose levels. It is more formally known as "impaired glucose tolerance" or "impaired fasting glucose," depending on which test is used to ascertain the condition. According to the ADA, the condition of pre-diabetes "almost always" exists prior to the full development of type 2 diabetes. Research has also shown that if a person takes action to manage his or her blood glucose when he or she has pre-diabetes, the individual can delay or prevent type 2 diabetes from ever developing.

In summary, a lifestyle of high sugar intake is a major risk factor for the development of pre-diabetic and type 2 diabetic states. The rise of industrialization has, for many Americans, wiped out the ability of attaining nature-based whole foods from the land, which the evolution of the human body has come to rely on to maintain homeostasis. As more sugar-laden processed and packaged (i.e., "convenient") foods displaced the wholesome diet, cases of type 2 diabetes began to increase sharply.

Insulin and Insulin Resistance

After a meal, the body's master metabolic hormone—insulin—is released from the pancreas into the bloodstream to transport the glucose from the bloodstream into cells that rely on the glucose for energy. In cases where the bloodstream is repeatedly inundated with glucose, the body's pancreatic cells release high levels of insulin to clear the glucose by cellular uptake. Inside the cell, glucose is either used for energy or stored for future use in the form of glycogen. However, insulin can lose its effectiveness over time, thereby leaving behind more glucose in the bloodstream.

"Glycemic response" is the pathway by which glucose reacts with insulin. Many foods contain carbohydrates that are broken down to glucose and rapidly absorbed from the intestine into the bloodstream. This rapid absorption of glucose leads to a high glycemic response or glycemic index (GI) and a consequent rapid secretion of insulin from the pancreas. Increased insulin levels are thought to be a key factor in the development of several diseases, including non-insulin dependent diabetes, cardiovascular disease, metabolic syndrome (Syndrome X), and insulin resistance.

Insulin resistance occurs when the normal amount of insulin secreted by the pancreas is unable to effectively mediate glucose uptake. To compensate, the pancreas secretes additional insulin. When the body's cells resist or do not respond to even high levels of insulin, glucose builds up in the blood resulting in high blood sugar. Even individuals being treated with oral medication or insulin injections to control their blood glucose levels can have higher than normal blood insulin levels due to insulin resistance.

More and more people in the United States are becoming obese, physically inactive, or both. Obesity and physical inactivity aggravate insulin resistance. Also, people who are insulin resistant typically have an imbalance in their blood lipids. They have an increased level of triglycerides (fat) and a decreased level of HDL ("good") cholesterol. Imbalances in total fat and HDL cholesterol increase the risk for heart disease. These findings have heightened awareness of insulin resistance and its impact on health.

Almost all individuals with type 2 diabetes mellitus ("diabetes")—and many with hypertension, cardiovascular disease, and obesity—are insulin resistant. These diseases and conditions have been predominantly found in highly industrialized countries with improved economic status, such as the United States. However, the prevalence of high sugar/high calorie foods has spread these diseases to rapidly developing economies like India and China. In the United States, these diseases and conditions are among the leading contributors to morbidity and mortality. Approximately 20-25% of the "healthy" population may be insulin resistant.

There are no outward physical signs of insulin resistance. A glucose tolerance test, during which insulin and blood glucose are measured, can help determine if someone is insulin resistant. There are also two different tests medical personnel may use to determine whether an individual has pre-diabetes: the fasting plasma glucose test (FPG) or the oral glucose tolerance test (OGTT). The blood glucose levels measured after these tests determine whether the individual has a normal metabolism, or whether the individual has pre-diabetes or diabetes. If an individual's blood glucose level is abnormal following the FPG, the individual has impaired fasting glucose (IFG). If an individual's blood glucose level is abnormal following the OGTT, the individual has impaired glucose tolerance (IGT).

Body Mass Index (BMI) and Waist to Hip Ratio

Body mass index is one measurement that factors in obesity as a marker for metabolic syndrome. However, due to the variability in the overall distribution of excess fat in the body, and the associated risk of cardiovascular diseases depending upon body type, ethnicity, regional variations, eating habits, etc., BMI was found to be insufficient to completely define the presence of metabolic syndrome. Therefore, to encompass a larger population with different body types and risks for metabolic syndrome, the waist to hip ratio was introduced as a more clinically relevant indicator.

A waist to hip ratio of >0.9 in men and >0.85 in women, a BMI of >30, or a combination of both are used as the basis to diagnose metabolic syndrome. Waist circumference is directly related to all-cause mortality when adjusted for BMI, highlighting the importance of waist to hip ratio.

Dyslipidemia

High levels of plasma triacylglycerols are considered as a significant risk factor for diagnosis of metabolic syndrome. Equally important is the levels of LDL and HDL. Low levels of plasma HDL and high levels of plasma LDL are more important for a positive diagnosis of metabolic syndrome. More specifically, the presence of small, dense LDL and triacylglycerol-rich remnant proteins is a clear indication of added risk factors for cardiovascular diseases.

High plasma triacylglycerol levels and insulin resistance have been found to co-exist in non-diabetic or prediabetic individuals, indicating some link between insulin resistance and dyslipidemia. Even in the wide range of plasma triacylglycerol levels (59-546 mg/dl) found in healthy individuals, there is a direct co-relation between increased secretion of hepatic VLDL-triacylglycerols, insulin resistance and the resultant hyperinsulinemia, clearly indicating the strong link between dyslipidemia and hepatic malfunction.

A lipoprotein profile with low levels of HDL and high levels of LDL (and more specifically high levels of VLDL) is a typical atherogenic lipoprotein profile indicating a high risk of atherosclerosis. Considering the link between plasma triacylglycerol and insulin resistance, the combined existence of these factors increases the risk of cardiovascular diseases and metabolic syndrome.

Hypertension

Another important risk factor related to metabolic syndrome is high blood pressure or hypertension. Hypertension is a chronic medical condition that may be classified as either primary (no underlying medical cause) or secondary (high blood pressure resulting from another condition). The prevalence of hypertension has reached epidemic proportions. It is estimated that 43 million people in the United States have hypertension or are taking antihypertensive medication, which is almost 24% of the adult population. Persistent hypertension is one of the risk factors for strokes, heart attacks, heart failure and arterial aneurysm, and is a leading cause of chronic renal failure. Even moderate elevation of arterial blood pressure leads to shortened life expectancy.

There is a complicated connection between hypertension and metabolic syndrome. As many as one-third of patients suffering from hypertension have metabolic syndrome, as defined by the ATP-III criteria. Hypertensive patients with metabolic syndrome exhibit an increased prevalence of hypertension-induced organ damage, left ventricular hypertrophy and atherosclerosis compared to patients with hypertension alone. The presence of both conditions results in a worsened long-term prognosis and heightened risk of cardiovascular and all-cause death.

Metabolic Syndrome—Treatments

The insulin resistance and pre-diabetes associated with metabolic syndrome can develop into type-2 diabetes. Once type-2 diabetes develops, it continues to progress despite added efforts to maintain plasma glucose levels as low as possible. Therefore, early diagnosis and treatment of metabolic syndrome is extremely important. It is equally as important to prevent the development of core metabolic syndrome and its related disorders.

Traditional approaches have focused mostly on the prevention or treatment of individual of metabolic syndrome-related components, disorders or symptoms (e.g., insulin resistance, hypertension or high plasma lipid profile, obesity, etc.) rather than treatment of the underlying syndrome itself. Pharmacologic intervention for prevention or treatment of metabolic syndrome-related disorders includes insulin secretogogues like tolbutamide, sulfonylureas, metformin, etc.; glucose uptake enzyme inhibitors like acarbose, and drugs which affect insulin sensitivity like troglitazone, etc.

Alpha-glucosidase inhibitors are oral anti-diabetic drugs that work by preventing the digestion of complex carbohydrates (such as starch). Complex carbohydrates are normally converted into simple sugars (monosaccharides) which can be absorbed through the intestine. Alpha-glucosidase inhibitors are saccharides that act as competitive inhibitors of enzymes needed to digest the carbohydrates; specifically alpha-glucosidase enzymes in the brush border of the small intestines. Hence, alpha-glucosidase inhibitors reduce the impact of complex carbohydrates on blood sugar. They are used to establish greater glycemic control over hyperglycemia in type-2 diabetes, particularly with regard to postprandial hyperglycemia. They may be used as mono-therapy in conjunction with an appropriate diabetic diet and exercise, or they may be used in conjunction with other anti-diabetic drugs. Examples of alpha-glucosidase inhibitors include the drugs Acarbose, Miglitol, and Voglibose Inhibition of these enzyme systems reduces the rate of digestion of complex carbohydrates. Less glucose is absorbed because the carbohydrates are not broken down into glucose molecules. In diabetic individuals, the short-term effect of these drug therapies is to decrease current blood glucose levels. However, a long term effect is a small reduction in hemoglobin (AlC) level.

There are a number of difficulties associated with the use of alpha-glucosidase inhibitors. Since alpha-glucosidase inhibitors are competitive inhibitors of the digestive enzymes, they must be taken at the start of main meals to have maximal effect. Therefore, their effects on blood sugar levels require strict compliance with a dosing schedule. Because alpha-glucosidase inhibitors prevent the degradation of complex carbohydrates into glucose, the carbohydrates will remain in the intestine. In the colon, bacteria will digest the complex carbohydrates, thereby causing gastrointestinal side effects such as flatulence and diarrhea.

Alpha-amylase enzyme inhibitors are also used in the treatment of metabolic syndrome-related disorders. Alpha-amylase is a digestive enzyme that acts in the lumen of the small intestine to breakdown starch (complex carbohydrates) into smaller carbohydrate units that can subsequently be broken down into the simple sugar glucose. Glucose is absorbed directly into the bloodstream following its uptake by intestinal cells, resulting in a relatively rapid rise in serum glucose levels. Glucose is used by all cells of the body to fuel metabolism. Excess glucose, however, can be converted into fat and stored in adipose tissue.

Alpha-amylase inhibitors interfere with the action of alpha-amylase. By blocking the breakdown of starch, they reduce the absorption of starch calories. However, high amounts of amylase inhibitors may also cause diarrhea due to the effects of undigested starch in the colon.

SUMMARY OF THE INVENTION

In a first embodiment of this invention, there is provided a composition comprising an aqueous and ethanol soluble, whole cranberry-derived, stress adapted bioactive (SAB) ingredient profile, or residue thereof, which is enriched in polyphenolics-containing stress adapted bioactives (SABs). The composition is produced by drying an aqueous or non-aqueous leach juice of whole fruit-derived cranberry pomace or otherwise derived from an extract of whole fruit cranberry pomace. The extract or leach juice may be produced using a low-molecular weight polar solvent including at least one component selected from a group consisting of an alcohol, ester, ether, amine, aldehyde, acid and water. In preferred embodiments, the solvent may consist of water and/or an organic solvent of 1 to 6 carbons. In a related embodiment, the SAB ingredient profile is a liquid.

In related embodiments, methods are provided for reducing blood glucose levels, increasing insulin activity, inhibiting alpha-glucosidase activity, inhibiting alpha-amylase activity, and reducing blood pressure in an individual by administering a pharmaceutically effective amount of the whole fruit-derived, cranberry SAB ingredient profile enriched in polyphenolics-containing SABs to the individual.

In a related embodiment, a method is provided for reducing blood glucose levels in an individual with one or more symptoms of metabolic syndrome by administering a pharmaceutically effective amount of a whole fruit-derived, cranberry SAB ingredient profile enriched in polyphenolics-containing SABs to the individual In a related embodiment, a method is provided for reducing blood pressure in an individual with one or more symptoms of metabolic syndrome by administering a pharmaceutically effective amount of a whole fruit-derived, cranberry SAB ingredient profile enriched in polyphenolics-containing SABs to the individual.

In a related embodiment, there are methods for increasing insulin activity, inhibiting alpha-glucosidase activity and inhibiting alpha-amylase activity in an individual with one or more symptoms of metabolic syndrome by administering a pharmaceutically effective amount of a whole fruit-derived, cranberry SAB ingredient profile enriched in polyphenolics-containing SABs to the individual with one or more symptoms of metabolic syndrome.

In another embodiment, there is provided a liquid composition from cranberry pomace, prepared by concentrating aqueous cranberry ingredient profile from whole fruit-derived pomace, the liquid composition being enriched in polyphenolics-containing SABs.

In another aspect of the invention, there is provided a method for producing a whole fruit-derived cranberry ingredient profile enriched in polyphenolics-containing SABs, wherein the method comprises expressing a juice from whole cranberries to produce a cranberry pomace, leaching the pomace with a solvent to produce a soluble polyphenolics-containing SABs cranberry pomace extract, and drying the cranberry pomace extract to produce a powder. In related embodiments, the solvent is a low-molecular weight composition where the solvent is comprised of at least one component selected from a group consisting of water, alcohol, ester, ether, amine, aldehyde and acid. In still another embodiment, there is provided a method for using dried cranberry powder, produced as described herein, to reduce blood glucose level, increase insulin activity, inhibit alpha-glucosidase activity and/or inhibit alpha-amylase activity in an individual with one or more symptoms of metabolic syndrome by administering a pharmaceutically effective dosage to the individual.

In related embodiments of the invention, the cranberry pomace extract is dried by spray drying, lyophilizing (freeze drying), radiant zone drying, refraction window drying and combinations thereof.

In another aspect of the invention, there is provided a method for producing a liquid composition that comprises expressing juice from cranberries to produce a cranberry derived pomace, leaching the pomace with a solvent to produce a pomace leach juice, and concentrating said leach juice to produce a liquid composition enriched in polyphenolics-containing SABs.

In another aspect of the invention, a method is provided for producing a liquid composition that comprises expressing juice from cranberries to produce a cranberry pomace, leaching the pomace with a solvent to produce a pomace leach juice, passing the leach juice through a resin column that selectively binds to polyphenolics-containing SABs, washing the resin using a washing solvent to remove compounds other than the polyphenolics-containing SABs, eluting the column with an eluting solvent to enhance the polyphenolics-containing SABs in a resulting liquid. In further embodiments, the resulting liquid may be concentrated to produce a concentrated liquid composition. The concentrated liquid composition may be dried to obtain a concentrated powder.

BRIEF DESCRIPTION OF THE DRAWINGS

The foregoing features of the invention will be more readily understood by reference to the following detailed description, taken with reference to the accompanying drawings, in which.

DETAILED DESCRIPTION

Definitions

Figure 1:
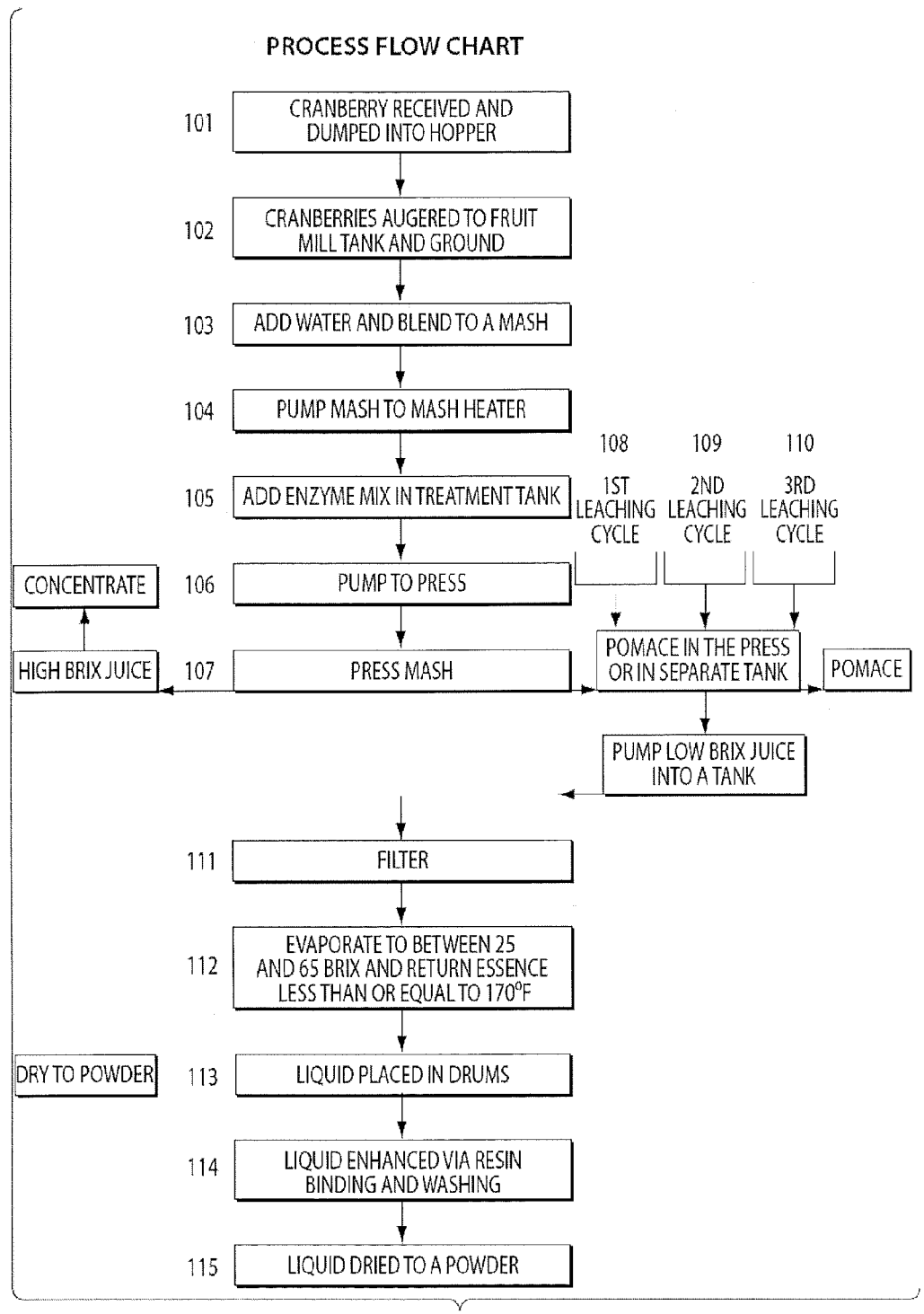
FIG. 1 is a flow chart of a process used to produce an aqueous and ethanol soluble powdered composition, in accordance with an embodiment of the present invention.

As used in this description and the accompanying claims, the following terms shall have the meanings indicated, unless the context otherwise requires:

"Whole fruit" as used herein, refers to all parts of the fruit, including skin, pulp, juice and components therein. Within the context of the application, "whole fruit" does not mean that the fruit is necessarily intact. As used herein "whole fruit" includes fruit that is broken, mashed, crushed, sliced, diced and puréed, as long as the components of the intact whole fruit are present, to some extent and have not been intentionally removed.

"Whole fruit-derived ingredient profile," "whole fruit-derived cranberry ingredient profile" or "whole cranberry-derived, SAB ingredient profile" as used herein, refer to a composition that has been partially isolated and purified from whole fruit, and includes extracts, leaches, residues, powders, liquids and other physical separations having the particular bioactivity of interest.

"Bioactive" and "bioactivity" as used herein refer to a biological activity, such as modulation of enzymatic activity, modulation of mRNA and/or gene expression, modulation of signal transduction, modulation of concentration levels of particular biomolecules in cells, tissue, fluids, organs and the like, or modulation of other activities associated with in vitro, ex vivo and in vivo biological systems. The activity may be directly or indirectly measured, monitored or determined, or may be monitored and/or assessed through downstream effects, physiological change, molecular change, subjective and objective monitoring of symptoms and wellness, or by other means, whether qualitative or quantitative, as appropriate.

"Polar solvent" or "polar solvents" as used herein refer to solvents having dipoles and polarity such that hydrogen bonding may occur, making such solvents capable of dissolving polar and charged molecules, to some extent, and making them miscible in water or soluble in water at some concentrations. In preferred embodiments, the terms refer to water or organic solvents having 1 to 6 carbons, including alcohols, esters, ethers, amines, aldehydes, ketones, acids and other polar solvents that are miscible in water or soluble in water at some concentrations. Examples of polar solvents, as used herein, include methanol, ethanol, propanol, glyceraldehyde, diols such as 1,6-hexane diol, triols such as glycerol, pyridine, cycyclohexylamine, piperidine, dimethylsulfoxide, acetone, dimethyl ether, diethyl ether, methyl acetate, ethyl acetate, ethylene glycol, t-butanol, isopropyl alcohol and the like.

There are no specific treatments for the core metabolic syndrome itself. The current approach involves lifestyle intervention, which includes changes in eating habits, exercise, etc. However, lifestyle intervention is not appropriate or successful for all individuals. Patient non-compliance and the presence of additional medical disorders or advanced age may limit its effectiveness. Pharmacologically, it is currently necessary to treat the individual components of the syndrome to reduce the risk level associated with each component. However, the pharmacological treatments described above are not effective or well tolerated for all individuals. Therefore, there is a need for a natural composition that is capable of treating the core metabolic syndrome and that may supplement or enhance known pharmacological treatments.

This invention relates to a composition and method for lowering blood glucose levels and/or glycosylated hemoglobin levels of individuals with one or more symptoms of metabolic syndrome by potentiating insulin activity and/or inhibiting alpha-glucosidase and/or alpha-amylase enzymes.

The composition that is employed in this invention exhibits insulin potentiating activity, i.e., it increases apparent insulin activity as measured by increased glucose uptake by cells. Improved insulin activity leads to decreased circulating insulin, which leads to lower blood glucose and lower glycosylated hemoglobin levels in individuals. It also has an effect on smoothing out fluctuations in glucose levels. The decrease in circulating insulin may further lead to a decrease in atherosclerosis. Total cholesterol, LDL-cholesterol and triglyceride levels in blood are decreased; and HDL-cholesterol levels are increased by administering the insulin potentiating agent.

The insulin potentiating agent is a natural composition derived from aqueous and ethanol soluble, whole fruit-derived ingredient profiles from food plants such as cranberries, and is safely consumed by humans. Therefore, the treatment of individuals with one or more symptoms of metabolic syndrome with such a natural whole fruit-derived composition has the advantage of minimizing or eliminating undesirable side effects. The use of this whole fruit composition in conjunction with conventional drug treatments such as an oral hypoglycemia agent or insulin permits the use of lower doses of the drug and/or decreased frequency of administration which decreases the side effects most commonly observed with these treatments.

The whole fruit-derived ingredient profile of cranberries is water and ethanol soluble, and is enriched in "Stress Adapted Bioactives" (SABs) containing polyphenolics. SABs are the spectrum of components produced by a plant as a response to the varied stresses experienced by the plant over its life and in post-harvest physiology, and such components are known to often possess specific and important physiologically relevant properties. Such an aqueous and ethanol soluble whole fruit-derived cranberry profile, enriched in polyphenolics-containing SABs, is made using a cranberry pomace, a combination of skins and seeds collected specifically through technologically advanced processes. Skins and seeds are the most important protective barriers of the fruit and protect fruit from various environmental stresses. Polyphenolics-containing SABs may be particularly concentrated in this pomace portion of cranberries. Such SABs can also be specifically induced under stress and developmental response, and targeted for enhancement via processing under stressed conditions, yet they remain viable and bioactive for human therapies and applications.

It is these stress-adapted (biologically, based on environmental and developmental needs) and stress-tolerant (technologically, thermally processed) cranberry SAB ingredients that are the most bioactive for human therapies and applications. For example, proanthocyanidins have been identified as the active components in cranberries that inhibit the adherence of uropathogenic *E. coli* to uroepithelial cells. Such SABs have been found to be enriched in aqueous- and ethanol-soluble polyphenolics from the skin, along with soluble oligosaccharides produced from skin polysaccharides that are solubilized by thermal processing from plant cell walls. Such components have more specific bioactive relevance due to their aqueous solubility, which enables them to modulate cell metabolite transfer activities and proton pump functionality, which is the basis of the redox biology of all living cells. Such components are concentrated in the whole ingredient profile of cranberries through specific usage of cranberries and various components of cranberries like pomace, seeds and skins which, during post harvest processing, are exposed to varied stresses to enhance the stress adapted bioactive without affecting the wholesome profile of the cranberries. Such a whole cranberry ingredient profile has been found to increase the functionality of redox reactions in yeast cells.

Figure 2:
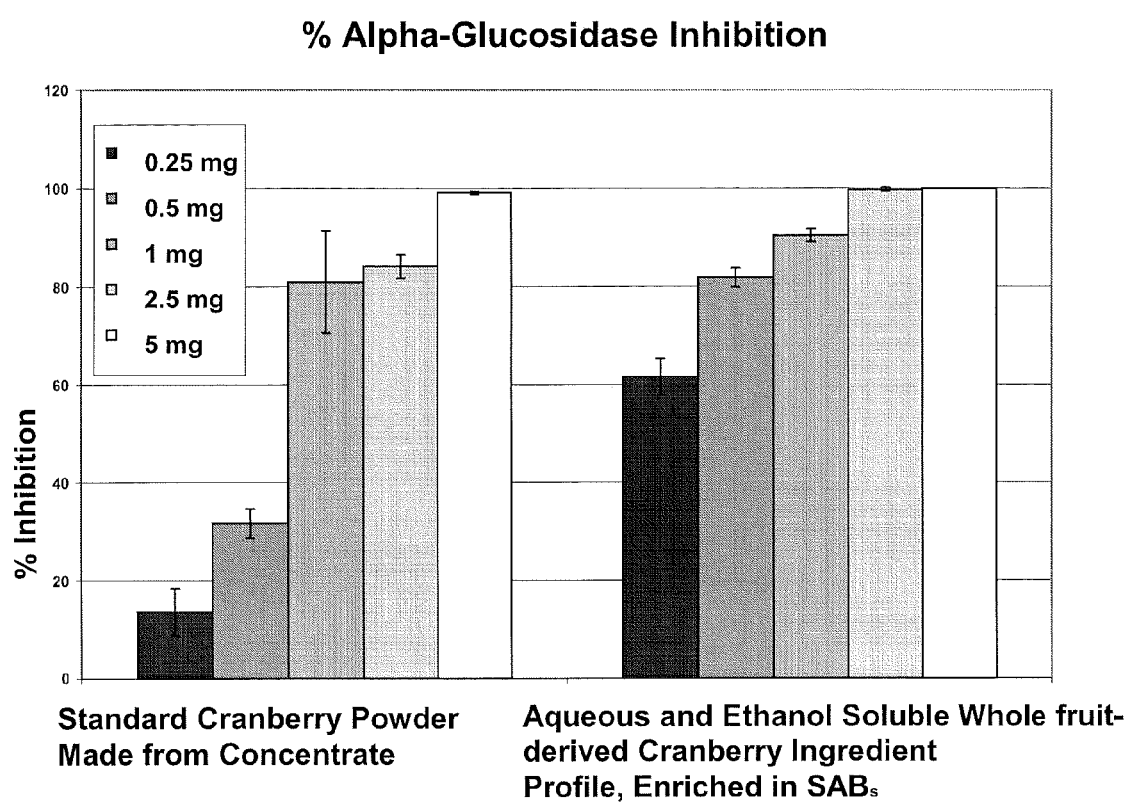
FIG. 2 is a chart showing alpha-glucosidase inhibitory activity of an aqueous and ethanol soluble whole fruit-derived cranberry ingredient profile enriched in polyphenolics-containing SABs, as compared with standard cranberry powder at different dosage levels.
Figure 3:
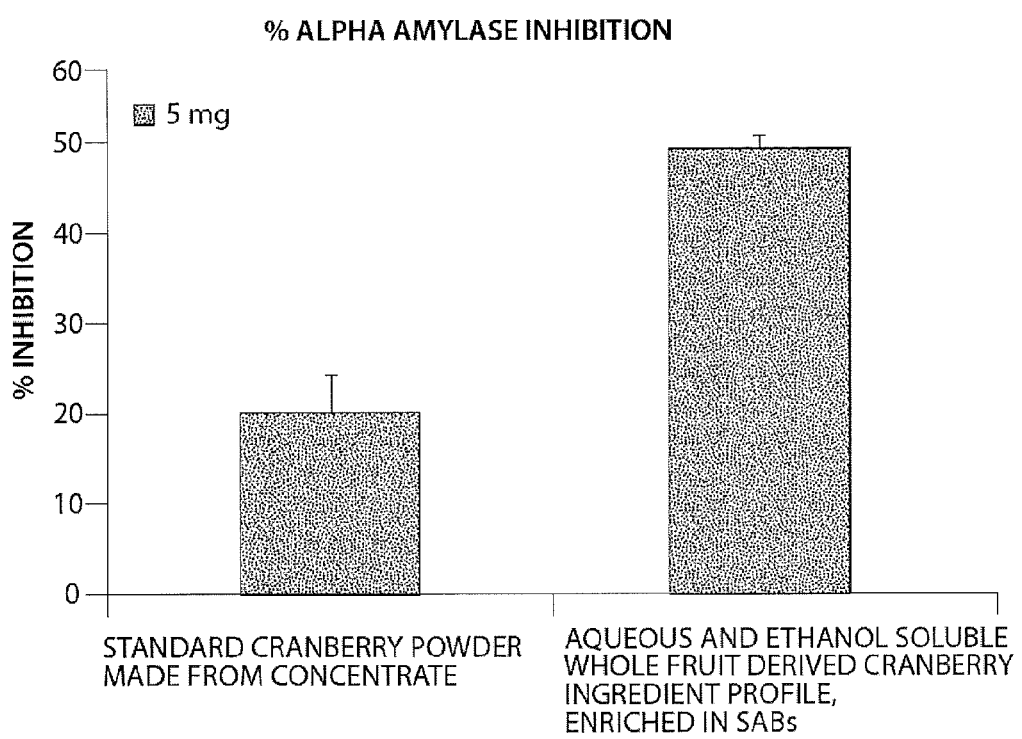
FIG. 3 is a chart showing alpha-amylase inhibitory activity of an aqueous and ethanol soluble whole fruit-derived cranberry ingredient profile, enriched in polyphenolics-containing SABs as compared with standard cranberry powder.
Figure 4:
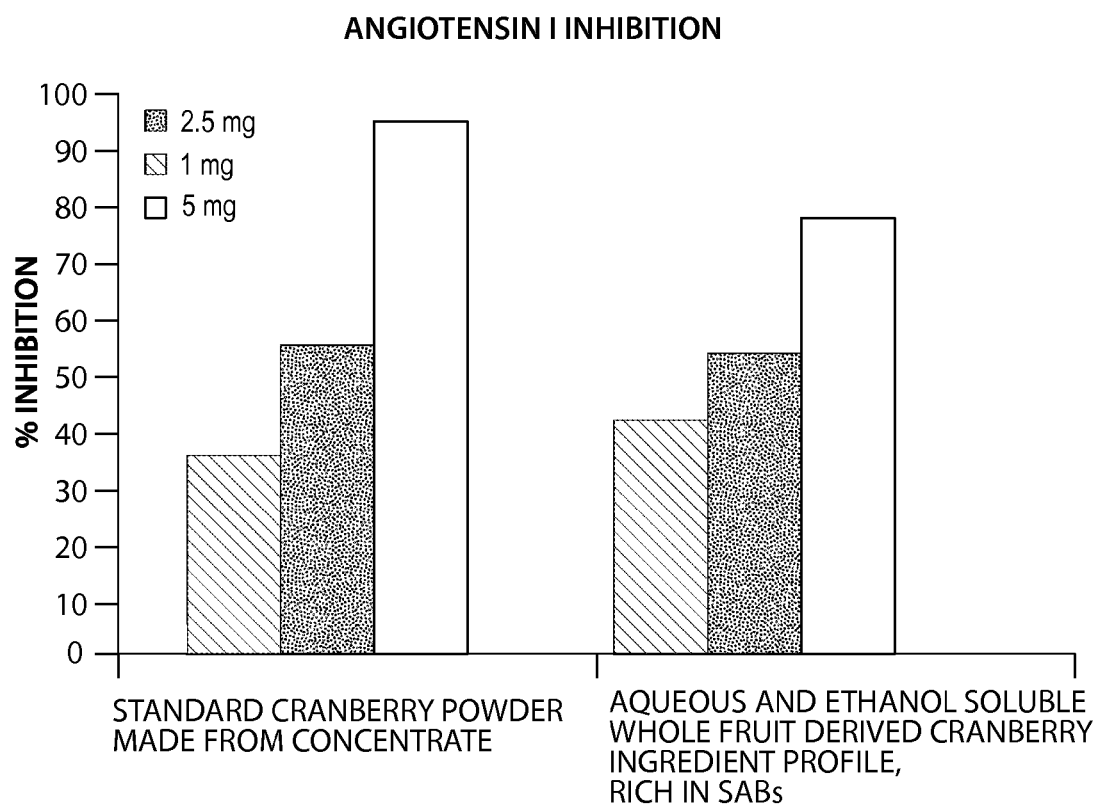
FIG. 4 is a chart showing ACE-I inhibitory activity of a whole fruit-derived cranberry ingredient profile, enriched in polyphenolics-containing SABs as compared with standard cranberry powder.
Figure 5:
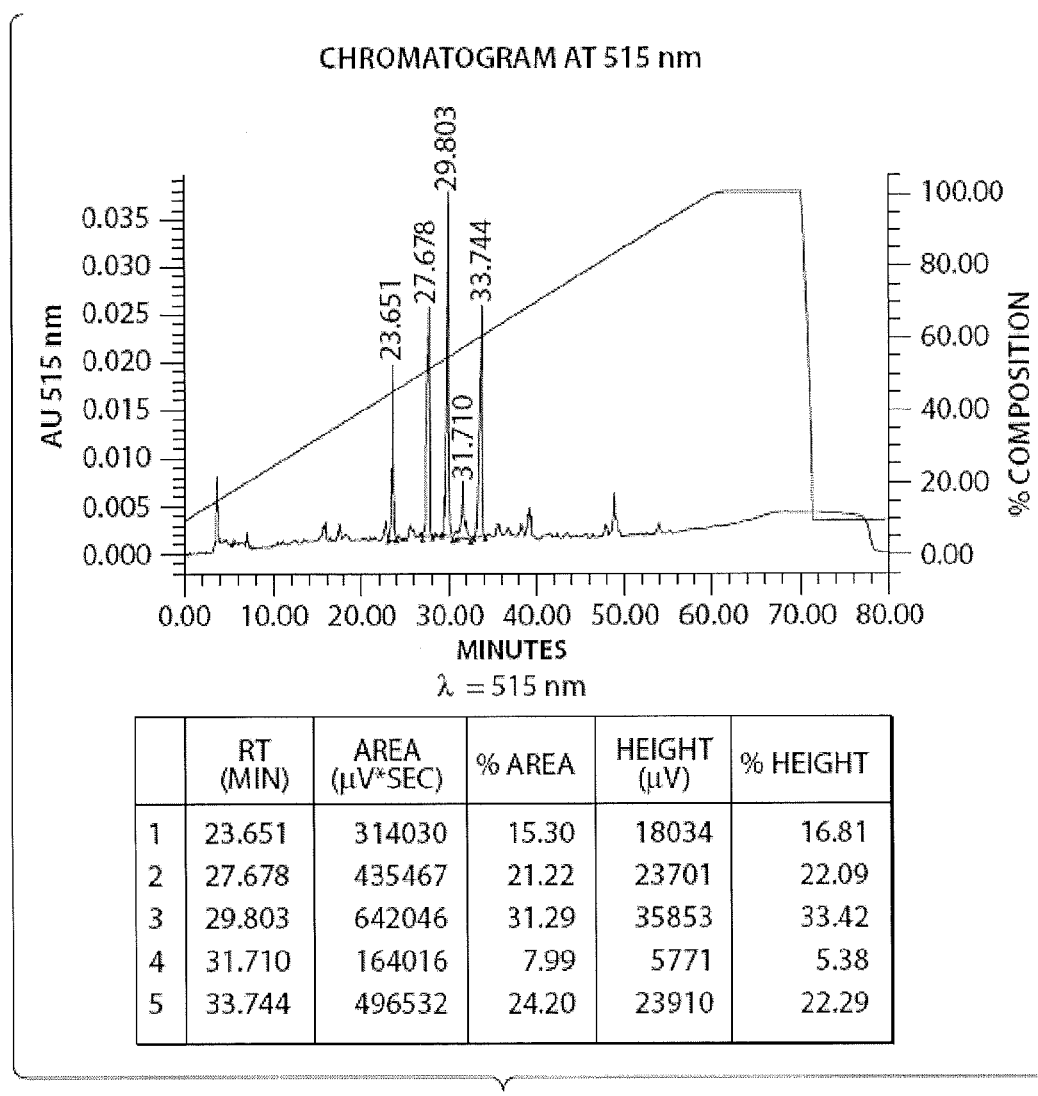
FIG. 5 is a chromatogram of a whole cranberry ingredient profile, enriched in polyphenolics-containing SABs at 515 nm.
Figure 6:
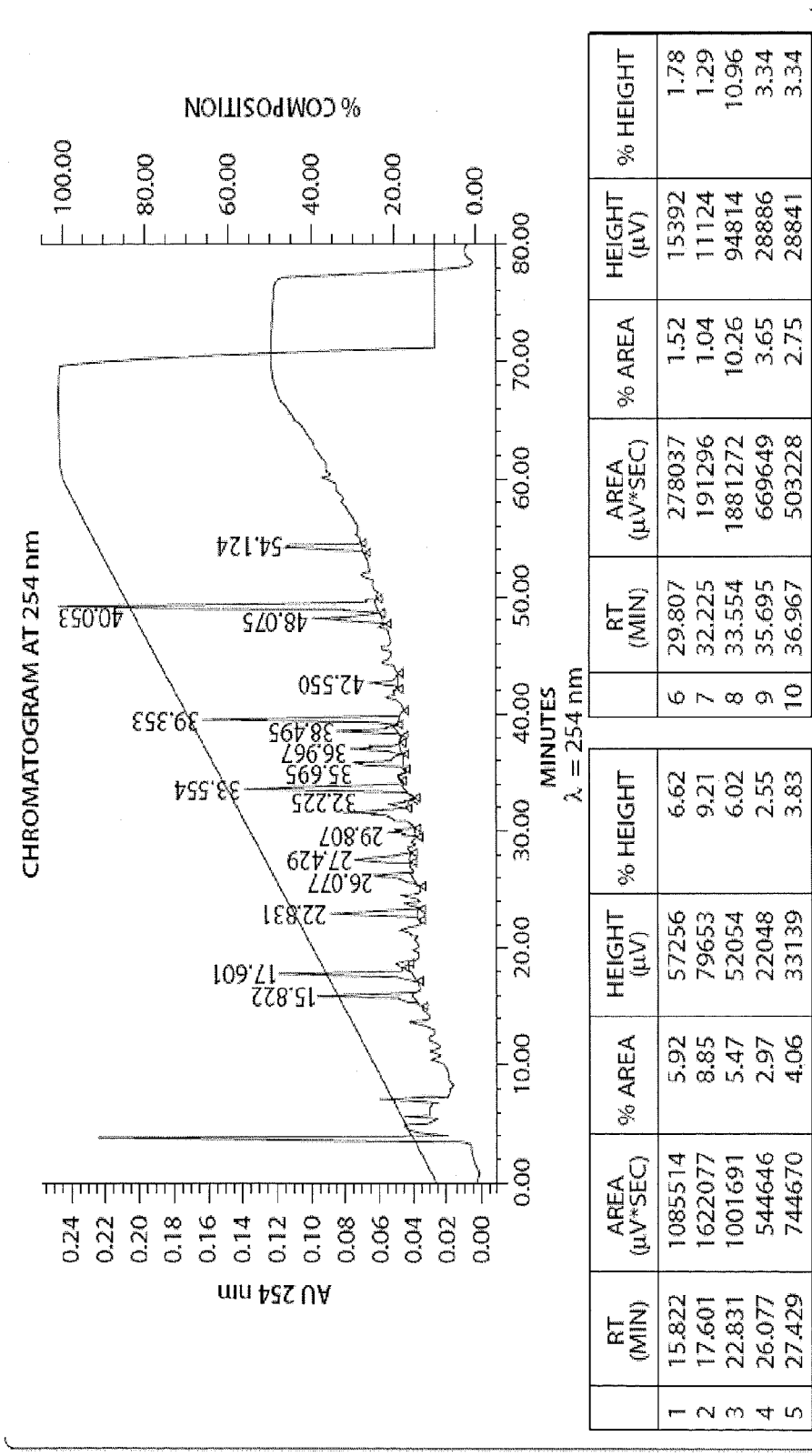
FIG. 6 is a chromatogram of a whole fruit-derived cranberry ingredient profile, enriched in polyphenolics-containing SABs at 254 nm.
Figure 7:
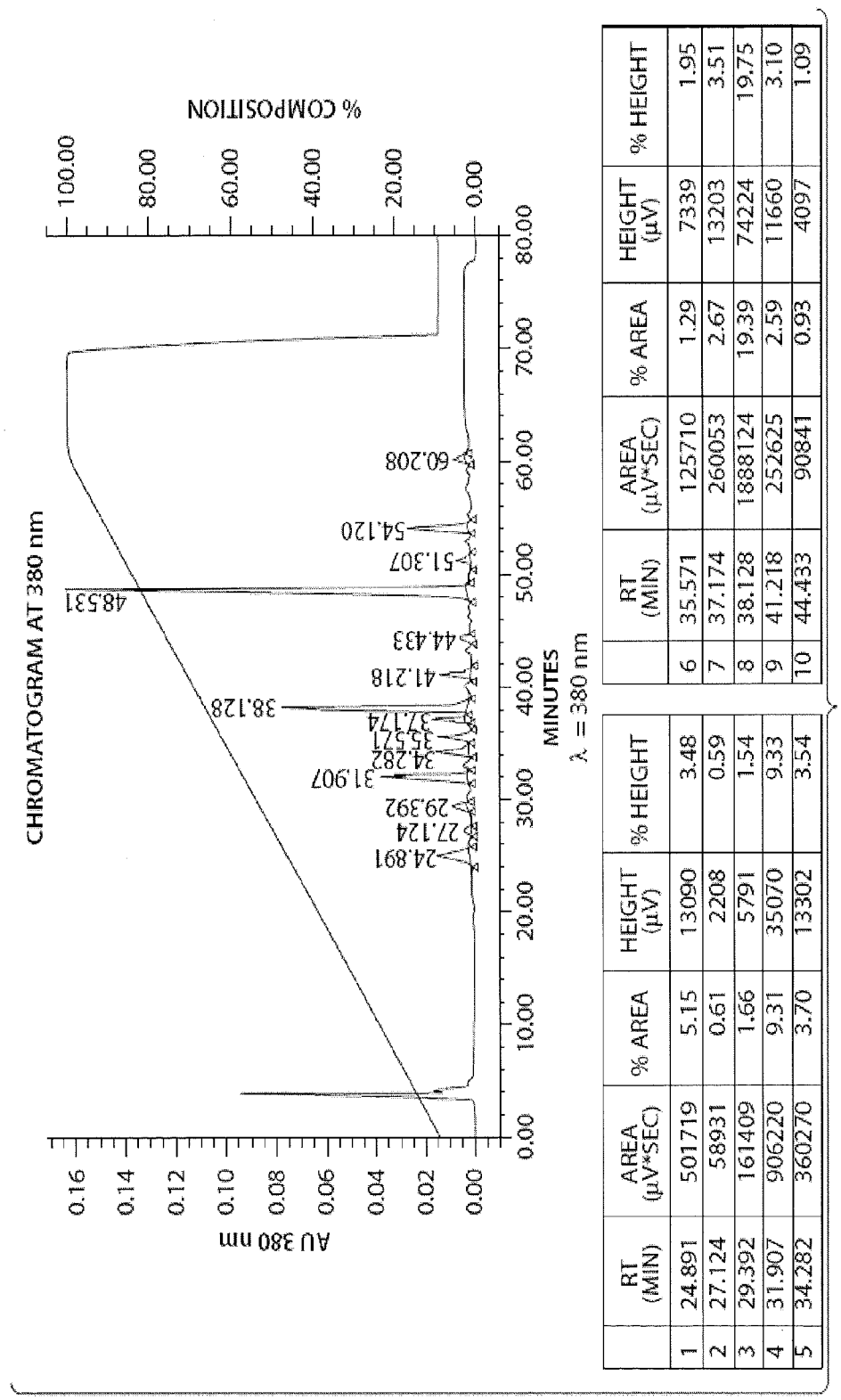
FIG. 7 is a chromatogram of a whole fruit-derived cranberry ingredient profile, enriched in polyphenolics-containing SABs at 380 nm.

Based on this understanding of soluble polyphenolics-containing SABs, and using the process illustrated in FIG. 1, cranberry pomace was leached to produce leach juice, and this juice was then concentrated to enrich the amount of polyphenolics-containing SABs per unit of weight. As shown in FIGS. 2-4, the effectiveness of the composition resulting from this process in inhibiting enzymes associated with metabolic syndrome, as compared to the effectiveness of the same dosage amount of whole fruit pomace, is unexpectedly and significantly higher, particularly at lower dosages. These results demonstrate the appreciable difference in the bioactivity and composition of the two substances, a difference that is attributable to the enriched level of polyphenolics-containing SABs per unit of weight.

These results are remarkable in that the presently disclosed and claimed compositions are obtained by aqueous extraction from pomace resulting after the juice from the cranberry has already been removed. Thus, after expressing the juice to leave only the pomace, subsequent aqueous extractions of the pomace result in an ingredient profile enriched for polyphenolics-containing SABs that exhibits significantly enhanced bioactivity, particularly against alpha-glucosidase and alpha-amylase at low concentrations.

What makes these results so surprising is that the compositions are derived from fruit product that had previously already been subjected to an aqueous expression of juice. One would not expect that a second extraction of material from which juice and aqueous components have already been removed exhibit greater bioactivity than standard extract obtained from juice concentrate.

The use of aqueous and ethanol soluble SABs, which are enriched in polyphenolics, allows for cellular protection from negative side effects of oxygen malfunction under diet-linked chronic disease pressure. Moreover, the cranberry pomace ingredient profile enriched in soluble polyphenolics and oligosaccharides has metabolites that modulate, in particular inhibit, specific pathways in the on-set towards diseases. Thus, one can envision the use of cranberry pomace-derived, SAB-containing leach extracts to manage oxygen-based dysfunction and inhibit specific structure-function targets associated with disease emergence.

Aqueous and ethanol soluble polyphenolics-containing SABs from whole fruit-derived cranberry fruit ingredient like pomace are a bridge between the two systems (protecting reactive oxygen-based dysfunction in cellular and tissue systems of cranberry and from this having the potential to inhibit oxygen dysfunction-based disease emergence such as type 2 diabetes in humans). Such cranberry ingredient profiles can manage oxidatively linked diseases, such as metabolic syndrome, through control of blood pressure (hypertension), type 2 diabetes, blood lipid profile and by inhibiting pathways that result in their increase. The disclosed cranberry pomace-derived ingredient profiles may also combat overall cellular breakdown from oxygen malfunction. Evidence for this is found in the use of a whole-fruit derived cranberry ingredient profile, enriched in polyphenolics-containing SABs, to modulate the inherent disease linked enzyme based pathways in animals, inhibit key glucose uptake enzymes, and increase the production and sensitivity of insulin receptor function (see Example 3). The cranberry pomace concentrate, rich in polyphenolics-containing SABs, may also modulate the endocrine linked pathway, which is associated with the feeling of satiety, and may therefore reduce diet trends towards obesity associated with symptoms of metabolic syndrome.

Individual polyphenolic components derived from non-cranberry plant species have been found to inhibit intestinal alpha-glucosidase, alpha-amylase and ACE-1 enzymes. Anthocyanins, as well as ellagitannins, have been shown to have this activity. As described in further detail below in connection with Example 2, cranberry-derived polyphenolics-containing SABs also inhibit alpha-glucosidase and alpha-amylase. In the present case, the disclosed cranberry ingredient profiles are proposed to act synergistically to improve postprandial hyperglycemia in type 2 diabetics, by slowing glucose absorption and by augmenting insulin action at the tissue level.

The whole fruit-derived cranberry ingredient profile liquid compositions prepared using cranberry pomace, free of solid debris, may be used directly as a glucose management agent, or the liquid composition may be dried to form a powder. The liquid or powder can then be incorporated into a variety of basic materials for administering in the form of a liquid, powder, tablets, or capsules. Such formulations may then be administered to individuals with hyperglycemia and/or other related disorders linked to metabolic syndrome, to decrease blood glucose and glycosylated hemoglobin levels.

In one embodiment a method is provided for treating hyperglycemia in an individual with symptoms of hyperglycemia, the method comprising administering to the individual a therapeutically effective amount of a cranberry pomace-derived composition as described below in various embodiments. An effective amount of the composition is the amount sufficient to provide a blood glucose response and may be determined empirically for each individual by monitoring long term glycemic control, because individual responses to treatment may vary, as is well known to those of skill in the art of hyperglycemia and associated metabolic syndrome. Dosages can be adjusted up or down depending on the response of the hyperglycemic individual. The effective amount will vary depending upon several factors, including, but not limited to, the age and weight of the disease state treated, how advanced the disease state is, the general health of the individual, the severity of the symptoms, whether the composition of this invention is being administered alone or in combination with other therapies, the incidence of the side effects and the like is reduced.

Several different methods are employed for establishing the response to treatment of an individual with hyperglycemia or one or more symptoms of the associated metabolic syndrome and for monitoring the amount of the composition to be administered. Measurement of serum glycosylated proteins, such as hemoglobin, is the most reliable method for assessing long term glycemic control in people with diabetes. Hemoglobin A (1c) was originally postulated to reflect the simple mean plasma glucose level over a certain period. Considering the erythrocyte life span, glycosylated hemoglobin was thought to be uniformly accumulated in erythrocytes over 120 days. However, theoretical and experimental evidence demonstrate that following a consistent drop in blood glucose, the HbA (1c) changes rapidly in the first one to two months followed by a steady-state level after four months. Seventy-five percent (75%) of the HbA(1c) level is proportional to the changes in blood glucose over the first two months. Two hour fasting blood glucose levels and serum insulin measurements are other methods which can be used to establish the effectiveness of treatment in with the composition and to monitor the amount of the composition administered. Blood glucose, hemoglobin A1C and insulin levels of individuals are measured at time zero and every thirty days by methods known to those skilled in the art.

Embodiments of the present invention as liquid or powder compositions may also find use in lowering total cholesterol, LDL-cholesterol and triglycerides levels, and in increasing HDL-cholesterol levels.

FIG. 1 is a flow chart of a process used to produce a powder composition with soluble stress-adapted bioactives, in accordance with an embodiment of the present invention. In step 101, whole raw cranberries ("cranberries") are received and placed into a hopper. Next, the cranberries are augered to a fruit mill tank and ground into pieces (step 102). Water is added (step 103) in a ratio to the cranberries of between 0.4:1 and 1:1 (water:cranberries) and then mixed to produce a mash. The mash is then pumped through a mash heater (step 104) to a treatment tank and heated to a temperature of between 90 and 130 degrees Fahrenheit. The mash is then treated with a depectinizing enzyme in a quantity of 0.1% to 0.3% in (step 105) where the mash sits for a time period ranging from 60 to 180 minutes.

After the mash and depectinizing enzyme have set, the depectinized mash is pumped to a press (step 106) and pressed (step 107) producing a high BRIX juice stream in the range of 3 to 9 BRIX which is then further evaporated and concentrated to yield 50 BRIX cranberry juice concentrate. This high BRIX juice may be used as a beverage or for other purposes.

The remaining extract of whole fruit-derived "pomace" material in the press may be leached with water in a ratio of 1:1 to 1:2 (pomace:water) and heated to a temperature between 125 to 220 degrees Fahrenheit for a period of time between 20 to 120 minutes (step 108). In alternative embodiments of the invention, the pomace may be leached with a polar solvent. In either case, leaching the cranberry pomace produces an aqueous and ethanol soluble, whole cranberry ingredient profile. After this initial leach, a low BRIX juice ranging from 0.3 to 2 BRIX is transported to a holding tank. The same leach cycle may be repeated a second and third time (steps 109 and 110) and the low BRIX juice transported to the holding tank. The leach cycle may also be repeated with different combinations of solvents.

Once the low BRIX juice has cooled in the holding tank, it is filtered to remove any large solid particles (step 111) and concentrated through an evaporator to a BRIX level of between 25 and 65 (step 112) and placed into drums (step 113). The resulting liquid composition is enriched in aqueous and ethanol soluble, polyphenolics-containing SABs that are useful to treat metabolic syndrome. Next, the liquid composition may be transformed into a powder or residue through freeze drying, spray drying, refractive window drying, or radiant zone drying. Alternatively, the liquid composition can be further processed in step 114 by contacting the liquid with a resin in a resin column, such as Amberlite high surface area/small pore resins produced by Rohm and Haas, that selectively bind polyphenolic compounds such as proanthocyanidins. The resin may then be washed with a solvent to remove non-SAB compounds, then eluted with an eluting solvent to elute the SABs enriched in polyphenolics. In this manner, the concentration of pharmaceutically and functionally active SABs in the liquid composition may be enhanced.

Finally, the liquid aqueous and ethanol-soluble whole fruit-derived cranberry ingredient profile, enriched in polyphenolics-containing SABs, may be processed by drying the liquid composition to a powder or residue in step 115. This may be accomplished by spray drying, freeze drying, refractive window drying and combinations thereof.

The embodiments of the invention described above are intended to be mere examples. Numerous variations and modifications will be apparent to those skilled in the art. All such variations and modifications are intended to be within the scope of the present invention as defined in any appended claims.

The following examples are presented as illustrations, not limitations:

EXAMPLE 1

Composition of the Aqueous- and Ethanol-Soluble Whole Fruit-Derived Cranberry Ingredient Profile, Enriched in Polyphenolics-Containing SABs Cranberry profile powder, rich in aqueous and ethanol soluble SABs enriched in polyphenolics prepared using the method outlined above was analyzed using HPLC. It was passed through a C-18 column and various end detectors were used to identify the chemical compounds. The polyphenolics-containing SABs were observed at 254 nm, 515 nm and 380 nm as seen in FIGS. 5, 6, 7, and 10 which includes glycosides of quercetin, myrecitin, kaempferol, anthocyanins, proanthocyanidins and several other unidentified components.

Figure 8:
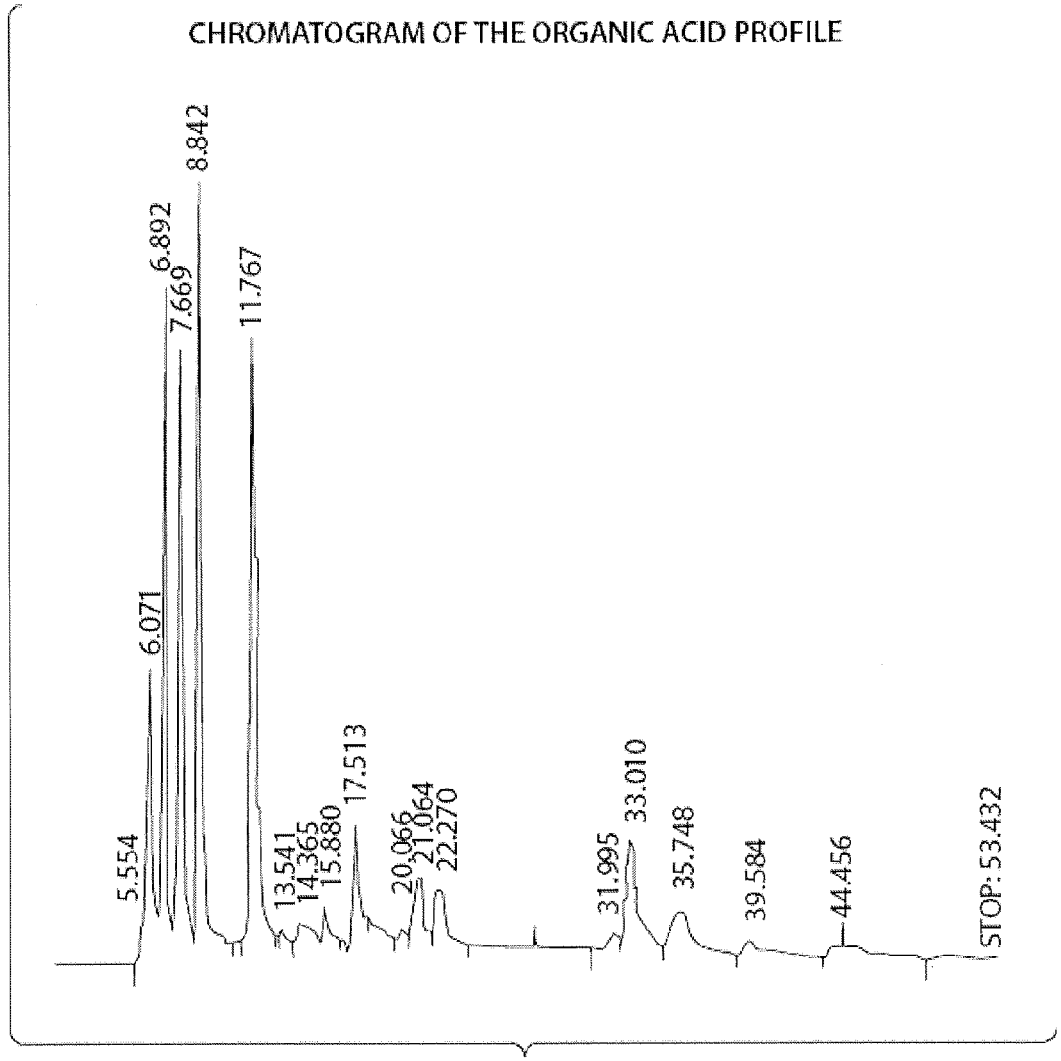
FIG. 8 is a chromatogram of organic acids present in a whole fruit-derived cranberry ingredient profile, enriched in polyphenolics-containing SABs.
Figure 9:
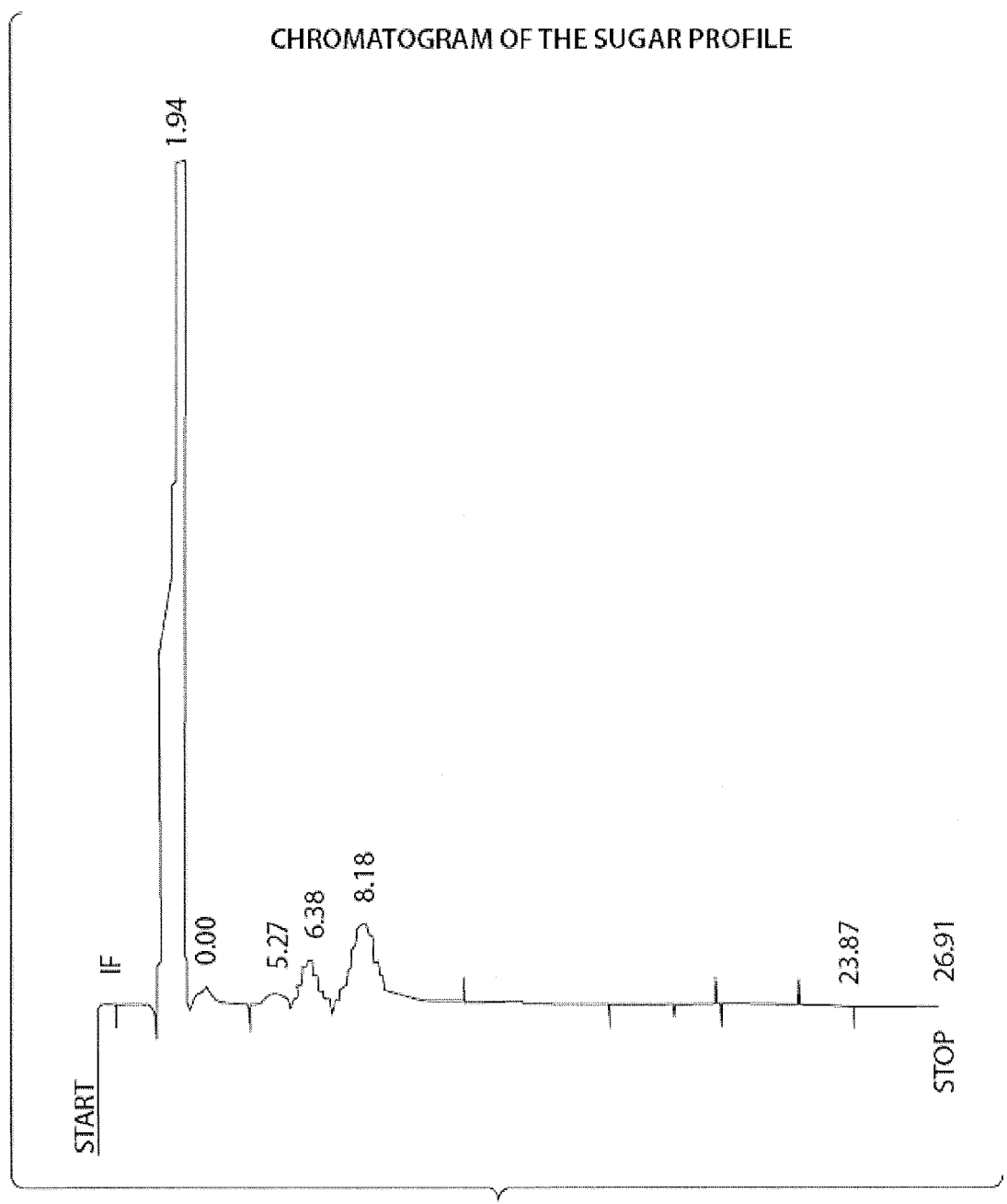
FIG. 9 is a chromatogram of sugars present in a whole fruit-derived cranberry ingredient profile, enriched in polyphenolics-containing SABs.
Figure 10:
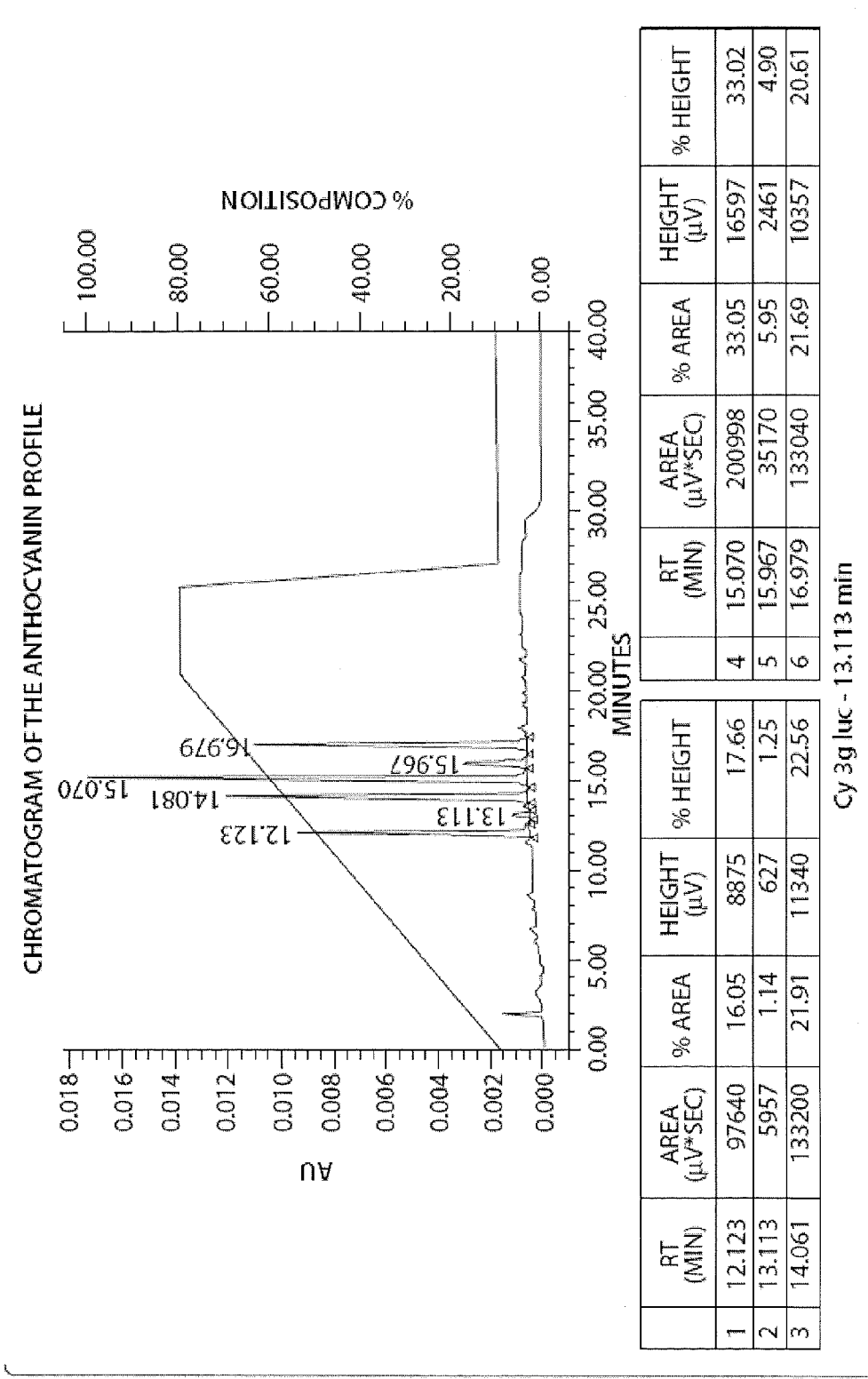
FIG. 10 is a chromatogram of the anthocyanin profile of a whole fruit-derived cranberry ingredient profile, enriched in polyphenolics-containing SABs.

Cranberry profile powder, enriched in aqueous and ethanol soluble polyphenolics-containing SABs was also analyzed for sugar (FIG. 8) and organic acid content (FIG. 9). Glucose and fructose being the major sugars present. Organic acids like citric, quinic and malic acid are present.

EXAMPLE 2

In Vitro Studies and Methodology

Standard cranberry powder, and aqueous and ethanol soluble whole fruit-derived cranberry ingredient profile, enriched in polyphenolics-containing SABs, were evaluated for their inhibitory activity to alpha-glucosidase, alpha-amylase, and ACE-1 enzymes. The aqueous and ethanol soluble whole fruit-derived cranberry ingredient profile, enriched in polyphenolics-containing SABs was found to be more effective than standard cranberry juice powder as an inhibitor of alpha-glucosidase, alpha-amylase and ACE-1 enzymes and the inhibition appears to be dose dependent.

Alpha-Glucosidase Inhibition Assay

Alpha-glucosidase activity was assayed by using 50 μL of water soluble supernatant of sample, enriched polyphenolics-containing SABs cranberry powder and 100 μL of 0.1 M phosphate buffer (pH 6.9) containing alpha-glucosidase solution (1 U/ml) and was incubated in 96 well plates at 25° C. for 10 min. After preincubation, 50 μL of 5 mM p-nitrophenyl-alpha-D-glucopyranoside solution in 0.1 M phosphate buffer (pH 6.9) was added to each well at timed intervals. The reaction mixtures were incubated at 25° C. for 5 min. Before and after incubation, absorbance readings were recorded at 405 nm by microplate reader (Thermomax, Molecular device Co., Sunnyvale, Calif.) and compared to a control which had 50 μL of buffer solution in place of the aqueous sample. The alpha-glucosidase inhibitory activity was expressed as % inhibition and was calculated as follows:

$$\% \text{ inhibition} = \left[ \frac{\Delta A_{405}^{Control} - \Delta A_{405}^{Extract}}{\Delta A_{405}^{Control}} \right] \times 100$$

The results comparing the inhibitory activity of the whole fruit-derived cranberry profile, enriched in polyphenolics-containing SABs, with standard cranberry juice powder are shown in FIG. 2. Table 1 shows an $IC_{50}$ comparison (n=12) from an alpha-glucosidase inhibition assay comparing cranberry extract of the invention with acarbose, a standard commercially available alpha-glucosidase inhibitor.

TABLE 1

| | $IC_{50}$ Data Summary (μg/ml) | |
|---|---|---|
| | Acarbose | Whole fruit-derived Cranberry Ingredient Profile, Enriched in Polyphenolics-containing SABs |
| Mean | 395.83 | 94.06 |
| Standard Deviation | 36.08 | 12.31 |
| Relative Potency | | 4 times that of acarbose |

Alpha-Amylase Inhibition Disk Assay

Eight hundred microliters of each water soluble supernatant of enriched polyphenolics-containing SAB cranberry powder from different dilutions (1×, 2×, 4×) was added to 200 μL of porcine pancreatic alpha-amylase (PPA) solution equivalent to 1000 U in 20 mM sodium phosphate buffer, pH 6.9. One hundred microliters of this solution was added to 0.5 in. sterile paper disk (Midwest Scientific, Valley Park, Mo.) placed at the center of Petri plates containing a medium that consisted of 5 g of agar and 5 g of starch in 500 ml of distilled water. The plates were sealed with parafilm and allowed to stand for 3 days at room temperature. Subsequently, 5 ml of iodine stain solution (5 mM iodine in 3% potassium iodide) was added to each plate and allowed to stand for 15 min. Excess iodine stain was drained, and the diameter of the clear zone was measured and used to calculate the amylase inhibitory activity. Control samples had only the PPA solution added to the paper disk. Results were reported as % amylase inhibition=[(diameter of the control−diameter of samples)/diameter of the control]×100. To make the comparison of amylase inhibitory activity between different research groups and laboratories possible, we adopted a convention of reporting the amylase inhibition index, which is defined herein as the ratio of the amylase inhibition (diameter) of the control sample to the amylase inhibition of the test sample. Values above 1 indicate amylase inhibition. A graph comparing values of the whole fruit-derived cranberry profile, enriched in polyphenolics-containing SABs, with the standard cranberry juice powder is shown (FIG. 3).

Angiotensin-1 Inhibition Assay

Angiotensin-1 (ACE-1) inhibition was assayed by modifying a method developed by Cushman and Cheung (1971). The substrate hippuryl-histidyl-leucine (HHL) and ACE-1 from rabbit lung (EC 3.4.15.1) were used. Fifty microliters of water soluble supernatant of enriched polyphenolics-containing SAB cranberry powder of different solutions (1×, 2×, 5×) were incubated with 100 μL of 1 M NaCl-borate buffer (pH 8.3) containing 2-mU ACE-1 solution at 37° C. for 10 min. After preincubation, 100 μL of a 5-mU substrate (HHL) solution was added to the reaction mixture. Test solutions were incubated at 37° C. for 1 hr. The reaction was stopped with 150 μL of 0.5-N HCl. The hippuric acid formed was detected; the spectra were confirmed and quantified by high performance liquid chromatography (HPLC) method. Five microliters of the sample was injected using Agilent ALS 1100 autosampler into an Agilent 1100 series HPLC (Agilent Technologies, Palo Alto, Calif.) equipped with DAD 1100 diode array detector. The solvents used for gradient were (1) 10-mM phosphoric acid (pH 2.5) and (2) 100% methanol. The methanol concentration was increased to 60% for the first 8 min. and to 100% for 5 min., then was decreased to 0% for the next 5 min. (18 min. total run time). The analytical column used was Nucleosil 100-5C18, 250×4.6 mm inside diameter, with packing material of 5 μm particle size at a flow rate of 1 mL/min at ambient temperature. During each run, the chromatogram was recorded at 228 nm and integrated using Agilent Chemstation (Agilent Technologies) enhanced integrator for detection of liberated hippuric acid. Pure hippuric acid (purchased from Sigma Chemical) was used to calibrate the standard curve and retention time. The % inhibition was calculated by $$\% \text{ inhibition} = \left[ \frac{E^{Control} - E^{Sample}}{E^{Control} - E^{Blank}} \right] \times 100$$

Where $E^{Control}$ is ACE-1+HHL acid (substrate); $E^{Blank}$ is sample+HHL (substrate); and $E^{Sample}$ is sample+ACE-1+HHL acid (substrate). A graph comparing inhibition of the whole fruit-derived cranberry ingredient profile, enriched in polyphenolics-containing SABs with the standard cranberry juice powder is shown (FIG. 4).

The results, as demonstrated in FIGS. 2, 3, and 4, indicate that cranberry compositions in accordance with embodiments of the present invention inhibit all three enzymes (alpha-glucosidase, alpha-amylase, ACE-1) which are key markers for diabetes management. Remarkably, the inhibition levels of the cranberry compositions in accordance with embodiments of the present invention are surprisingly much greater than that observed for comparable concentrations of standard cranberry extract from concentrate. In particular, note the levels of inhibition of alpha-glucosidase by cranberry compositions described herein at 0.25 mg and 0.5 mg, as seen in FIG. 2, wherein the percent inhibitions are dramatically greater for the cranberry compositions of the invention, in a non-linear fashion, compared to that seen at the same concentrations of standard cranberry extract from concentrate. In fact, the percent inhibition at 0.25 mg is only about 12% for standard extract, compared to about 62% for the cranberry composition of the invention, and only about 30% for standard cranberry extract compared to about 82% for cranberry compositions of the invention at 0.5 mg.

Similarly, the level of inhibition of alpha-amylase by cranberry compositions of the invention compared to the same concentration of standard cranberry extract from concentrate, as seen in FIG. 3, jumps from about 21% for the standard extract to about 52% for the cranberry composition of the invention. Lastly, although not as pronounced a difference, the level of inhibition of ACE-1 by cranberry compositions of the invention at 1 mg compared to the same concentrations of standard cranberry extract from concentrate, as seen in FIG. 4, nonetheless increases from about 35% for the standard cranberry extract to about 42% for the cranberry composition of the invention.

In summary, as seen particularly in FIG. 2, but is also evident in FIG. 4, the dose-response inhibition curves of the embodiments of the invention are relatively linear, with greater percent inhibition observed at lower concentrations relative to the percent inhibition observed at the same concentrations for the standard extract from concentrate. In contrast, the dose-response curves for the standard cranberry extract from concentrate in FIGS. 2 and 4 are much less linear, exhibiting far less percent inhibition at the lower concentrations compared to the extracts that are embodiments of the invention.

Yeast Cell Assay

Excess oxidative stress in humans triggers a specific programmed cell death pathway, which leads to apoptosis. Such apoptosis of cells leads to aging and other inflammation and oxidation related diseases such as Type 2 diabetes. Similar mechanisms of cell apoptosis have been seen in yeast cells (*Saccharomyces cerevisiae*) when exposed to excess oxidative stress. *Saccharomyces cerevisiae* have been used to understand the antioxidant activity of botanical extract preparation of *Ilex paraguariensis* as it relates to human low density lipoprotein oxidation. Hence, a yeast cell model is used to understand the antioxidant effects of various components and their relevance for use in humans.

Yeast cells are generally killed when exposed to UV light at 254 nm within 8 min. This is due to the excess stress experienced by the cells which affects the functioning of the basic proton pump and intracellular proton modulation, which then affects overall homeostasis of the cells causing the cells to die under oxidative stress. When such cells are exposed to or pretreated with the whole fruit-derived cranberry ingredient profile, enriched in polyphenolics-containing SABs, before the UV treatment there is a marked improvement in their survival rate. The cells survive for as long as 20-25 min. This indicates the physiological significance of the enriched polyphenolics-containing SABs as modulators of the proton pump function and proton modulation.

EXAMPLE 3

In Vivo Studies

Methodology

Streptozotocin-induced diabetes: Streptozotocin is a fungal metabolite (*Streptomyces achromogenes*) and is selectively toxic to the beta cells of the pancreatic islets which produce the hormone insulin and is used to induce diabetes in animal models. Six to eight week old male Wistar rats are used to show how the cranberry composition enhances or mimics the action of insulin. Experimental procedures are carried out in accordance with IACUC (Institutional Animal Care and User Committee). All animals are housed in air conditioned room at 23±1° C. with 12 h light/dark cycle and are provided with standard purified diet AIN-93 and water ad libitum. Animals are weighed at baseline and at weekly intervals throughout the experiments. Also, at baseline and at specified time points, blood specimens are collected to measure glucose, insulin, cholesterol, LDL, HDL, lipase, SGOT, SGPT. At the end of the experiment, specimens from liver, heart, pancreas, kidney and muscle from representative animals from each group are harvested for histologic evaluations. For each study group approximately 9 rats are used.

Oral glucose tolerance test and insulin sensitivity index: Animals are fasted for 12 h in preparation for the oral glucose tolerance test (OGTT). Each rat is given, by oral gavage, a solution containing 40% glucose (1 g/kg body wt). Blood samples are taken at 0, 15, 30, 60, 120 and 240 minutes after gavage for the various measurements. The area under the curve for insulin is calculated using the trapezoidal method.

The insulin sensitivity index is calculated from the data of plasma glucose and insulin according to known formulas. It has been shown that results derived from the insulin sensitivity index correlate well with those from the euglycemic hyperinsulinemic clamp technique.

Prevention of Streptozotocin-induced Diabetes: Adult rats (10-12 weeks old; 9 rats per group) are fed either a control AIN-93 diet or one containing aqueous and ethanol soluble, whole fruit-derived cranberry profile, rich in high polyphenolics containing SABs (23.2 mg/kg) for two weeks. After two weeks on the control or extract containing diet, animals are fasted for 18-24 h and streptozotocin (STZ; 70 mg/kg) in 10 mM citrate buffer (pH4.5) is administered i.p. Age-matched controls receive a citrate buffer only (see treatments below). Blood glucose levels are monitored on alternate days post streptozotocin injection using an Accu-check blood glucose meter for 4 weeks. Rats with blood glucose levels >15 mM (200 mg/dl) for 2 consecutive samples are considered diabetic. Representative animals from the control and extract-fed groups are sacrificed and pancreas harvested for comparative histology.

Treatments:
1. AIN-93 Diet (Control)
2. AIN-93 Diet+Cranberry Composition
3. AIN-93 Diet+Streptozotocin (70 mg/kg; day 14)
4. AIN-93 Diet+Cranberry Composition+Streptozotocin (70 mg/kg; day 14)

SABs-enriched cranberry composition containing polyphenolics to reverse streptozotocin-induced diabetes: Six to eight week old rats (total of 27 animals) are fasted for 18-24 h and streptozotocin (STZ; 30 mg/kg) in 10.0 mM citrate buffer is administered i.v. through the tail vein. Age-matched controls receive a citrate buffer only. One week later, blood glucose levels are monitored on alternate days using an Accu-check blood glucose meter. Rats with blood glucose levels ≥15 mM (200 mg/dl) for 2 consecutive weeks are considered diabetic. Aqueous and ethanol soluble, whole fruit-derive cranberry profile, enriched in polyphenolics-containing SABs, is introduced into the diet of both hyperglycemic and matched control animals (see treatments below). After 6 weeks of Cranberry composition feeding, in vivo studies are carried out to assess the effects of Cranberry composition on glucose uptake and metabolism. Blood specimens are collected at baseline (before streptozotocin injection), before extract feeding, and after 6 weeks of Cranberry composition diet. Specimens are tested for glucose, insulin, cholesterol, LDL, HDL, SGOT, SGPT and lipase. Oral glucose tolerance test (OGTT) is evaluated on 5 animals per group. The same animals used for OGTT are sacrificed and tissues harvested for histology.

Treatments:
1. Control AIN-93 diet
2. Control AIN-93 diet+Streptozotocin (d 10)
3. Control+Cranberry Composition+Streptozotocin (d 10)

SABs-enriched cranberry composition containing polyphenolics for acutely increasing insulin sensitivity: Male Wistar rats (~250 g)(6/treatment) are used for this study. Experimental Type I diabetes mellitus are induced by a single intraperitoneal injection of freshly prepared STZ at a dose of 70 mg/kg in 50 mM citrate buffer (pH 4.5) after the rats are fasted overnight. Only diabetic animals (those with polyuria, glycosuria and hyperglycemia of ~20 mM glucose) 2-3 days post-induction are used in this experiment. Studies are carried out 1 week after STZ injection. STZ-diabetic rats are divided into the following treatments: (see treatments below).

1. Control—Oral gavage of tap water;
2. Oral gavage of SABs-enriched cranberry composition containing polyphenolics in aqueous solution (5.3 g/kg body weight);
3. Oral gavage of tap water plus insulin given at a dose of 9 nmole/animal ip;
4. Oral gavage of SABs-enriched cranberry composition containing polyphenolics in aqueous solution (5.3 g/kg body weight) plus insulin given at a dose of 9 nmole/animal ip;
5. Oral gavage of SABs-enriched cranberry composition containing polyphenolics in aqueous solution (5.3 g/kg body weight) plus insulin given at a dose of 1.26 nmole/animal ip;

Blood glucose concentrations are measured and then (zero time) the respective treatments are administered. Blood samples are collected by tail bleeding, and glucose measured at 30, 60, 90, 120, 150, 210 and 270 min.

SABs-enriched cranberry composition containing polyphenolics for reducing insulin resistance: Male Wistar rats (6 weeks of age) were randomly assigned into 4 groups (9 rats per group) as follows (see treatments below): 1) Control (starch based diet); 2) fructose-rich diet (AIN based diet containing 53% by weight of fructose, 0 kcal starch), 3) fructose-rich diet supplemented with 3.3 mg/kg of SABs-enriched cranberry composition containing polyphenolics, and 4) fructose-rich diet supplemented with 6.6 mg/kg of high polyphenolics containing SAB enriched cranberry composition. Food consumption is measured once weekly and fluid consumption is monitored every two days. An oral glucose tolerance test is performed at the end of week 6, on 4 animals per group (see below). At the end of the experiment, all animals are sacrificed and the organs (pancreas, liver, heart) harvested for tissue histological examination.

Treatments:
1. AIN-93 diet (Starch based)
2. Fructose-rich AIN-93 diet (53% fructose)
3. Fructose-rich AIN-93 diet+SABs-enriched cranberry composition containing polyphenolics (3.3 mg per kg diet) [HF+LC]
4. Fructose-rich AIN-93 diet+double SABs-enriched cranberry composition containing polyphenolics (6.6 mg per kg diet) [HF+MC]

Results

Figure 11:
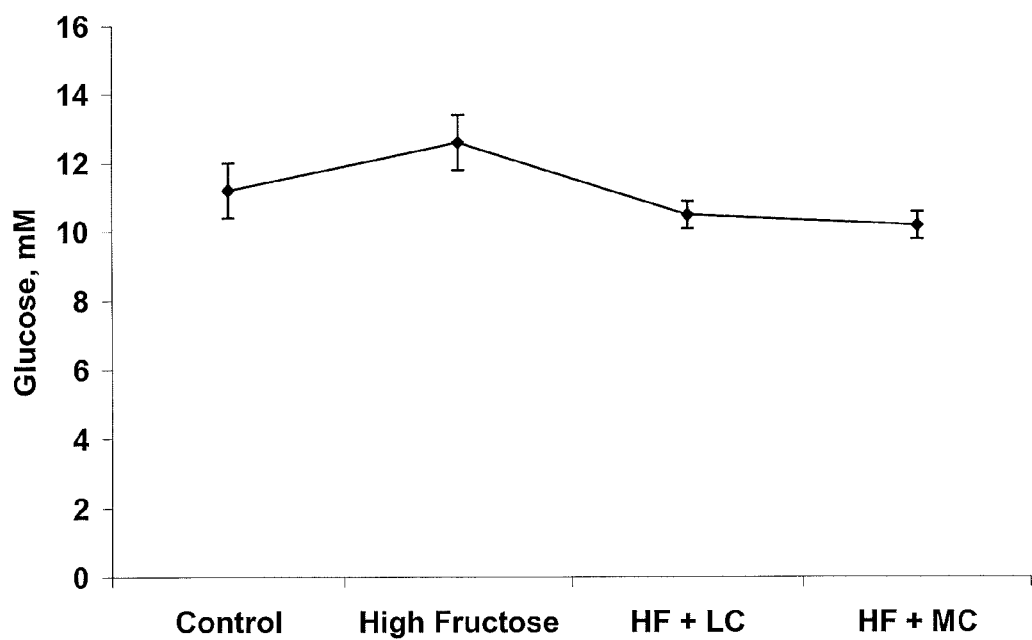
FIG. 11 is a graph showing fasting blood glucose levels in rats fed with high fructose diet compared to high fructose diets supplemented with SABs-enriched cranberry composition containing polyphenolics at two different dose levels (LC and MC).

Results from animal studies indicate that the various levels of supplementation did not have a straight line correlation for the parameters evaluated as part of the study. Fasting blood glucose level increased significantly in the high fructose group. Notably, supplementing the diet with compositions prepared in accordance with the process illustrated in FIG. 1 restored the fasting blood glucose levels to those seen in normal rats (FIG. 11). This effect was not incremental with the level of supplementation. Both levels had the same effect on fasting blood glucose level (FIG. 11), which might be due to saturation. Fasting insulin levels did not change significantly in any of the groups throughout the experiment. Table 2 shows the serum glucose, insulin and insulin homeostasis assessment scores in rats fed with high fructose diet and high fructose diets supplemented with SABs-enriched cranberry composition containing polyphenolics at two different dose levels (LC and MC)

TABLE 2

| Item | Control | High Fructose | HF + LC [c] | HF + MC [d] |
|---|---|---|---|---|
| Glucose, mM | 11.2 ± 0.8 [a,b] | 12.6 ± 0.8 [b] | 10.5 ± 0.4 [a] | 10.2 ± 0.4 [a] |
| OGTT [f] | 10457 ± 1234 | 13625 ± 1349 | 9472 ± 855 | 10466 ± 1336 |
| Insulin, mU/L | 44.9 ± 9.7 | 39.9 ± 4.8 | 31.0 ± 3.8 | 24.8 ± 6.2 |
| HOMA-IR [g] | 22.9 ± 6.2 | 22.8 ± 3.7 | 14.6 ± 1.9 | 11.8 ± 3.4 |
| HOMA-BCF [h] | 118.8 ± 22.7 | 88.2 ± 7.7 | 90.4 ± 12.3 | 71.2 ± 14.9 |
| QUICKI [i] | 0.78 ± 0.05 [a,b] | 0.76 ± 0.05 [a] | 0.91 ± 0.05 [a,b] | 1.12 ± 0.12 [b] |

Figure 12:
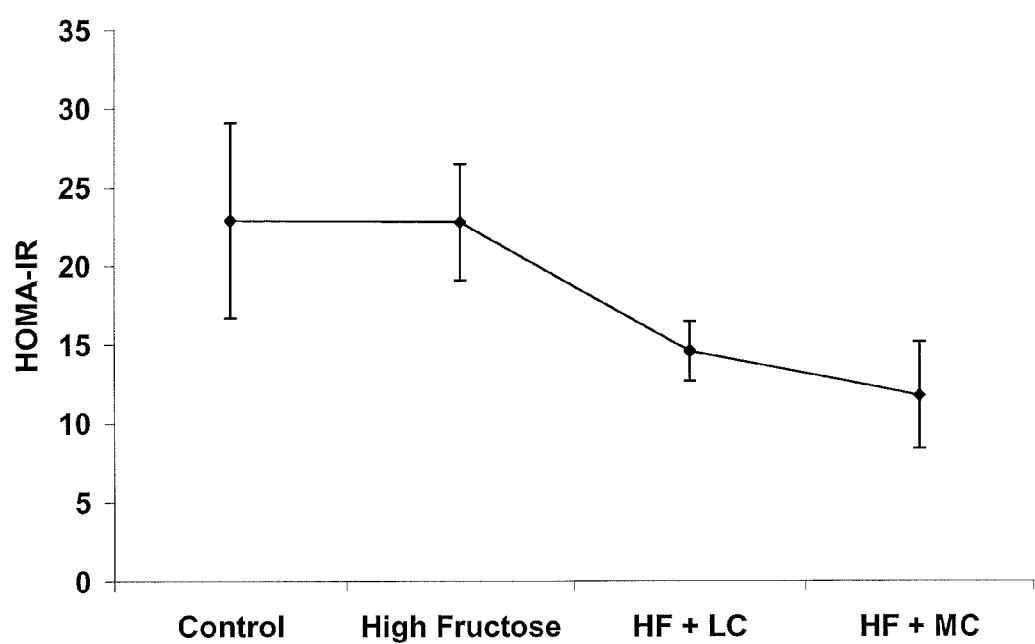
FIG. 12 is a graph showing the insulin resistance index (HOMA-IR) in rats fed with high fructose diet compared to high fructose diets supplemented with SABs-enriched cranberry composition containing polyphenolics at two different dose levels (LC and MC).
Figure 13:
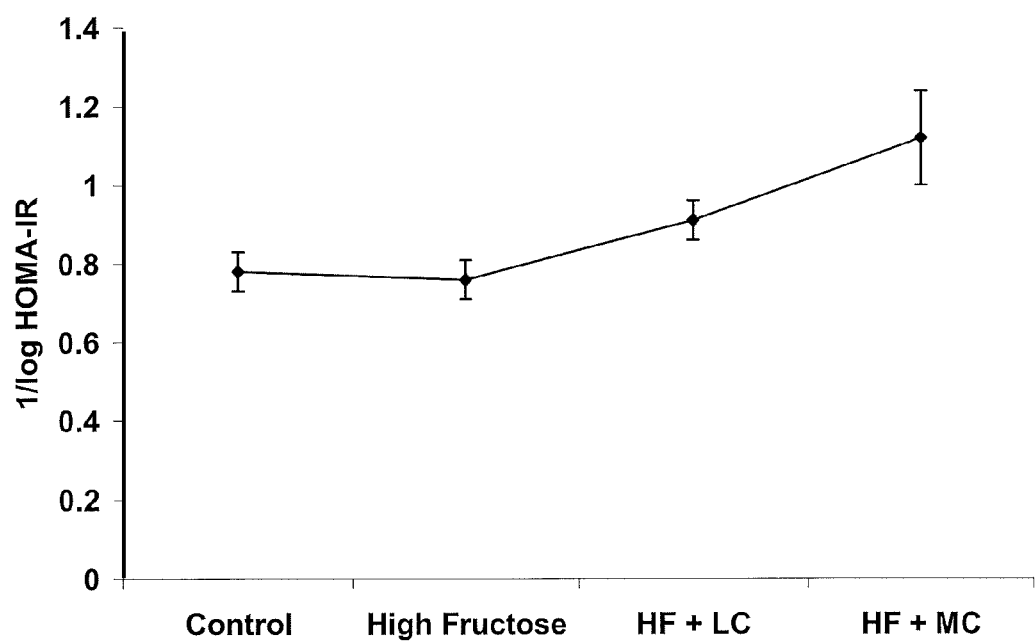
FIG. 13 is a graph showing the insulin sensitivity index (QUICKI) of rats fed with high fructose diet compared to high fructose diets supplemented with SABs-enriched cranberry composition containing polyphenolics at two different dose levels (LC and MC).

[a,b] Means without a common superscript are significantly different ($p < 0.05$).
[c] Low level of supplementation with high polyphenolics containing SAB enriched cranberry composition = 3.3 g/kg diet
[d] Medium level of supplementation with high polyphenolics containing SAB enriched cranberry composition = 6.6 g/kg diet
[f] Oral glucose tolerance test area under curve expressed as mg/100 mL × minutes$^{-1}$
[g] Homeostasis model assessment – Insulin resistance (HOMA-IR) = [Fasting glucose (mg/100 mL) – Fasting Insulin (μU/mL)]/405
[h] Homeostasis model assessment – β-cell function (HOMA-BCF) = Reciprocal of HOMA-IR
[i] Quantitative insulin sensitivity check index (QUICKI) = 1/log HOMA-IR The insulin resistance index indicated that the low and medium levels of supplementation led to a significant decrease in insulin resistance (FIG. 12). The insulin sensitivity index (QUICKI) indicated some dose dependency with increased supplementation (FIG. 13), but this too showed signs of saturation.

Analyzing the rats after completion of the study for organ and tissue weights indicated that there were no major differences in the various groups. Table 3 shows the final body and tissue weights in rats fed with high fructose diets and high fructose diets supplemented with SABs-enriched cranberry composition containing polyphenolics at two different dose levels (LC and MC).

TABLE 3

| Item | Control | High Fructose | HF-LC | HF-MC | P< |
|---|---|---|---|---|---|
| Final Weight, g | 493.6 ± 14.4 | 429.0 ± 14.4 | 464.0 ± 14.4 | 455.9 ± 14.4 | NS |
| Heart, g | 1.79 ± 0.07 | 1.62 ± 0.07 | 1.63 ± 0.07 | 1.58 ± 0.07 | NS |
| Kidney, g | 3.26 ± 0.15 | 3.23 ± 0.15 | 3.30 ± 0.15 | 3.32 ± 0.15 | NS |
| Heart, % BW | 0.36 ± 0.01 | 0.38 ± 0.01 | 0.35 ± 0.01 | 0.35 ± 0.01 | NS |
| Liver, % BW | 2.48 ± 0.11 | 2.75 ± 0.11 | 2.73 ± 0.11 | 2.96 ± 0.11 | 0.06 |
| Kidney, % BW | 0.66 ± 0.02[a] | 0.75 ± 0.02[b] | 0.71 ± 0.02[ab] | 0.73 ± 0.02[b] | 0.04 |
| Serum Triglycerides, mg/dL | 76.1 ± 11.6 | 107.6 ± 13.7[b] | 81.1 ± 8.0 | 68.3 ± 8.5[a] | 0.085 |

Figure 14:
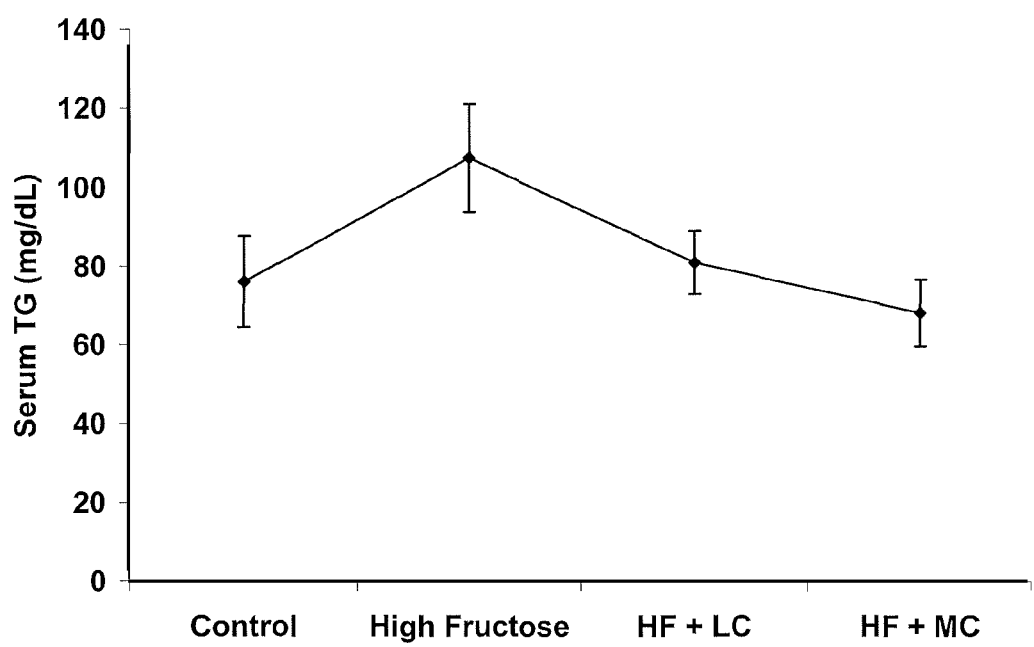
FIG. 14 is a graph of the serum triglycerides in rats fed with high fructose diet compared to high fructose diets supplemented a SABs-enriched cranberry composition containing polyphenolics at two different dose levels (LC and MC).

Serum triglycerides were significantly higher in the rats fed with high fructose diet as compared to the rats with normal diet (FIG. 14). This effect was completely neutralized by supplementing the high fructose diet with compositions prepared in accordance with the process illustrated in FIG. 1. This effect was not incremental with the level of supplementation, indicating a saturation effect.

Figure 15:
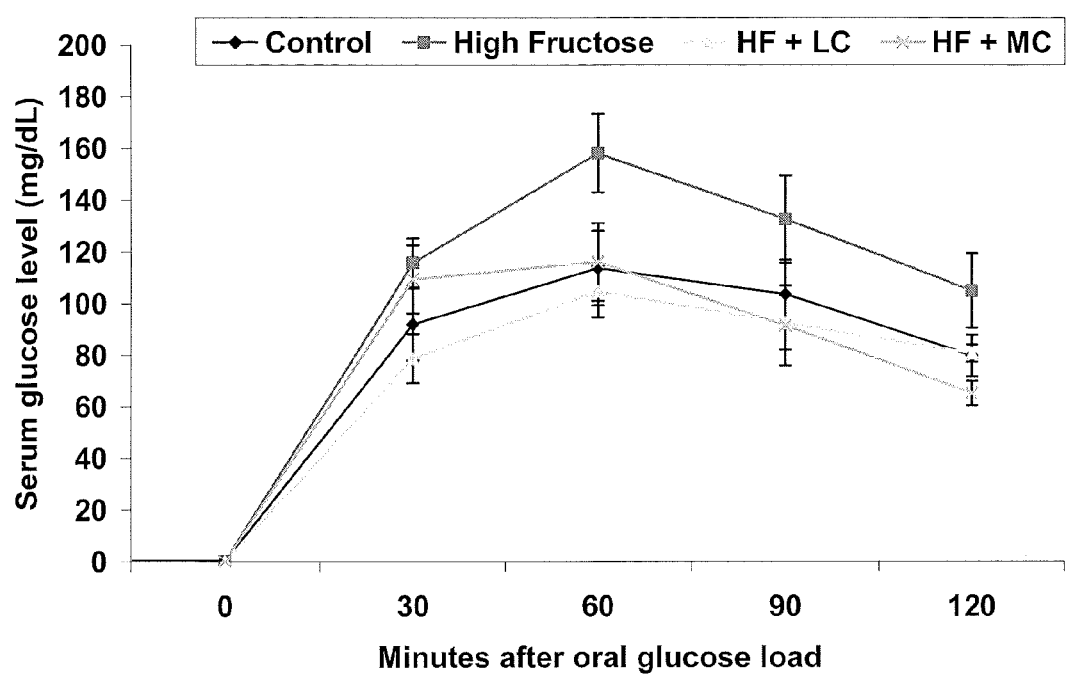
FIG. 15 is a graph of an Oral Glucose Tolerance Test conducted at the end of week 6 in rats fed with high fructose diet compared to high fructose diets supplemented with SABs-enriched cranberry composition containing polyphenolics at two different dose levels (LC and MC).

Oral Glucose Tolerance Test (OGTT) conducted at the end of week 6, indicated that the high fructose diet fed rats had significantly higher blood glucose levels than the control after 30 minutes and up to 120 minutes after the glucose challenge. As illustrated in FIG. 15, this effect was reduced to levels similar to those seen in control rats by supplementing the high fructose diet with low and medium levels of compositions prepared in accordance with the process illustrated in FIG. 1.

What is claimed is:

1. A composition for treating diabetes consisting essentially of a therapeutically effective amount of an extract from cranberry pomace, wherein said cranberry pomace is obtained by a process of:
   a) grinding whole cranberries into pieces of cranberries;
   b) mixing the pieces of cranberries with a first quantity of water to produce a mash;
   c) treating the mash with a depectinizing enzyme to yield a depectinized mash that comprises cranberry juice and cranberry pomace;
   d) separating the cranberry pomace from the cranberry juice;
   e) mixing the cranberry pomace with a second quantity of water to produce leach juice;
   f) separating the leach juice from the cranberry pomace;
   g) concentrating the leach juice to produce the extract from cranberry pomace.

* * * * *